United States Patent
Nolan et al.

(10) Patent No.: US 8,679,858 B2
(45) Date of Patent: Mar. 25, 2014

(54) LANTHANIDE MASS DOTS: NANOPARTICLE ISOTOPE TAGS

(75) Inventors: Garry P. Nolan, San Francisco, CA (US); Erin F. Simonds, Stanford, CA (US); Sean C. Bendall, San Mateo, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/348,512

(22) Filed: Jan. 11, 2012

(65) Prior Publication Data

US 2012/0178183 A1   Jul. 12, 2012

Related U.S. Application Data

(60) Provisional application No. 61/461,017, filed on Jan. 11, 2011.

(51) Int. Cl.
*G01N 33/563* (2006.01)
*G01N 33/553* (2006.01)

(52) U.S. Cl.
USPC .................. 436/512; 436/513; 436/525

(58) Field of Classification Search
USPC ........................ 436/512, 513, 525
See application file for complete search history.

(56) References Cited

U.S. PATENT DOCUMENTS

| | | | |
|---|---|---|---|
| 4,205,952 A | 6/1980 | Cais | |
| 5,492,814 A * | 2/1996 | Weissleder | 435/7.25 |
| 5,514,602 A * | 5/1996 | Brooks et al. | 436/525 |
| 5,773,292 A | 6/1998 | Bander | |
| 5,872,013 A * | 2/1999 | Leunissen et al. | 436/525 |
| 6,235,540 B1 * | 5/2001 | Siiman et al. | 436/518 |
| 6,468,808 B1 * | 10/2002 | Nie et al. | 436/524 |
| 6,548,264 B1 * | 4/2003 | Tan et al. | 435/7.21 |
| 7,108,915 B2 | 9/2006 | Adams et al. | |
| 7,135,296 B2 | 11/2006 | Baranov et al. | |
| 7,611,907 B2 * | 11/2009 | Dickson et al. | 436/525 |
| 7,772,013 B2 * | 8/2010 | Robinson et al. | 436/524 |
| 8,026,108 B1 * | 9/2011 | Huo et al. | 436/525 |
| 2004/0058389 A1 * | 3/2004 | Wang et al. | 435/7.1 |
| 2005/0266417 A1 | 12/2005 | Barany et al. | |
| 2008/0176334 A1 | 7/2008 | Baranov et al. | |
| 2008/0258159 A1 | 10/2008 | Jun et al. | |
| 2009/0098663 A1 * | 4/2009 | Han et al. | 436/525 |
| 2009/0220792 A1 | 9/2009 | Ying et al. | |
| 2010/0144056 A1 * | 6/2010 | Winnik et al. | 436/501 |
| 2010/0151472 A1 * | 6/2010 | Nolan et al. | 435/6 |
| 2011/0124131 A1 * | 5/2011 | Lee et al. | 436/525 |
| 2011/0311970 A1 * | 12/2011 | Shachaf et al. | 435/6.11 |
| 2013/0171646 A1 * | 7/2013 | Park et al. | 435/6.11 |

OTHER PUBLICATIONS

Alivisatos, A.P. "Semiconductor clusters, nanocrystals, and quantum dots", Science (1996), 271:933-937.*

(Continued)

*Primary Examiner* — Shafiqul Haq
*Assistant Examiner* — Gary E Hollinden
(74) *Attorney, Agent, or Firm* — Bozicevic, Field & Francis LLP; Pamela J. Sherwood

(57) ABSTRACT

Compositions and methods are provided for the use of nanoparticles, which may be referred to herein as mass dots, as mass tags for probes such as antibodies, aptamers, nucleic acids, etc. in multiplexed bioassays with ICP-MS detection.

16 Claims, 11 Drawing Sheets

(56) References Cited

OTHER PUBLICATIONS

Shachaf, C.M. et al., "A novel method for detection of phosphorylation in single cells by surface enhanced raman scattering (SERS) using composite organic-inorganic nanoparticles (COINs)", PlosOne (2009), 4(4):1-12.*

Lou; et al., "Polymer-Based Elemental Tags for Sensitive Bioassays", Angew Chem Int Ed Engl. (2007), 46(32):6111-6114.

Ornatsky; et al., "Development of analytical methods for multiplex bio-assay with inductively coupled plasma mass spectrometry", J Anal At Spectrom (2008), 23(4):463-469.

Vancaeyzeele; et al., "Lanthanide-Containing Polymer Nanoparticles for Biological Tagging Applications: Nonspecific Endocytosis and Cell Adhesion", J. Am. Chem. Soc. (2007), 129(44):13653-13660.

* cited by examiner

LANTHANIDE MASS DOTS: NANOPARTICLE ISOTOPE TAGS

FEDERALLY SPONSORED RESEARCH AND DEVELOPMENT

This invention was made with Government support under contract HV028183 awarded by the National Institutes of Health. The Government has certain rights in this invention.

BACKGROUND OF THE INVENTION

Conventional detection reagents for biological assays frequently consist of a binding moiety having specificity for the molecule of interest, conjugated to a moiety with enzymatic or optical properties. To date, these determinations are generally facilitated through the use of radiological, fluorescent or enzymatic tags.

Among methods of interest for analysis, flow cytometry provides the means for simultaneous multiparametric analysis of the physical and/or chemical characteristics of up to thousands of particles per second, and is routinely used for research and clinical diagnostic applications, including both particle analysis and particle sorting. The analysis of cells is of particular interest. Modern instruments usually have multiple lasers and fluorescence detectors. Increasing the number of lasers and detectors allows for simultaneous analysis of multiple labeled antibodies, and can more precisely identify a target population by their phenotypic markers.

In traditional flow cytometry, fluorescently labeled particles such as live cells, fixed cells, beads, etc. are individually distinguished and separated based on their fluorescence and light scatter characteristics. The phenotype of the particles can be further investigated after they are isolated. Such traditional flow cytometry methods are limited by the number of simultaneous parameters that can be measured on a single particle, and there are problems with overlap of fluorescence emissions during simultaneous measurement; and background fluorescence or enzymatic activity. As the number of simultaneous parameters increases, this spectral overlap severely convolutes analysis impinging on both the accuracy as well as sensitivity of the assay.

In alternative methods of detection, atomic mass spectrometry measurements have been used in conjunction with stable isotope tags of rare elements. Existing elemental tagging capture reagents for use in ICP-MS are based on chelators, such as ethylenediamine tetra-acetic acid (EDTA), tetraazacyclododecane-tetraacetic acid (DOTA) or diethylenetriaminepentaacetic acid (DTPA), for example a maleimide-functionalized polymer of DTPA, with an average length of between 10 and 30 monomers. Such protocols allow conjugation to a typical antibody of 6 or 7 polymers, thereby conjugating an average of 200 tagging isotope atoms per antibody. The sensitivity of this method is directly related to the number of elemental isotope tags per detection reagent molecule. The number of polymers that can be attached is limited to the number of disulfide bonds that can be broken on the immunoglobulin without disrupting its function. The number of metal chelating units that can be conjugated to a detection reagent is also limited because increased numbers can interfere with the detection reagent or induce nonspecific interactions and thus interfering or inducing high background in an assay.

Other existing nanocrystal labeling reagents include luminescent nanocrystals, also known as upconversion nanocrystals, quantum dots, luminescent nanocrystals, and Raman composite organic-inorganic nanoparticles (COINs), all of which were designed for optical or electromagnetic labeling. To achieve useful optical properties, the nanocrystals used in these products contain high-atomic mass dopants, such as cadmium, tellurium, selenium, europium, terbium, or neodymium, and contain undefined mixtures of these rare metals. The high-atomic mass dopants occupy otherwise useful channels of instrument detection. The mixed nature of the elements and their isotopes in these reagents makes them less desirable for atomic mass spectrometry measurement as it would dilute the signal, thus reducing sensitivity, as well as occupy multiple measurement channels per reagent that could otherwise be used as individual reporters.

There is interest in methods of analysis that provide for highly sensitive detection of molecules in biological assays, where multiple parameters can be simultaneously analyzed without signal overlap. The present invention addresses this issue.

Publications

U.S. Pat. No. 7,135,296 Baranov: Elemental analysis of tagged biologically active materials. Winnik et al., J. Anal. At. Spectrom. 2008; 23(4): 463-469, Development of analytical methods for multiplex bio-assay with inductively coupled plasma mass spectrometry. Winnik et al., Angew. Chem. Int. Ed. 2007; 46 (32): 6111-6114, Polymer-Based Elemental Tags for Sensitive Bioassays. Winnik et al., J. Am. Chem. Soc. 2007; 129(44): 13653-13660, Lanthanide-containing polymer nanoparticles for biological tagging applications: Non-specific endocytosis and cell adhesion; Thickett et al. (2010) Bio-functional, lanthanide labeled polymer particles by seeded emulsion polymerization and their characterization by novel ICP-MS detection. *Journal of Analytical Atomic Spectrometry* 25 (3):269-281; Abdelrahman et al. (2010) Lanthanide-Containing Polymer Microspheres by Multiple-Stage Dispersion Polymerization for Highly Multiplexed Bioassays (vol 131, pg 15276, 2009). *Journal of the American Chemical Society* 132 (7):2465-2465, 2010; Berger et al. (2010) Hybrid nanogels by encapsulation of lanthanide-doped LaF3 nanoparticles as elemental tags for detection by atomic mass spectrometry. *Journal of Materials Chemistry* 20 (24):5141-5150; Ornatsky et al. (2010) Highly multiparametric analysis by mass cytometry. *J Immunol Methods* 361 (1-2):1-20; Bandura et al. (2009) Mass Cytometry: Technique for Real Time Single Cell Multitarget Immunoassay Based on Inductively Coupled Plasma Time-of-Flight Mass Spectrometry. *Analytical Chemistry* 81:6813-6822

SUMMARY OF THE INVENTION

Elemental mass spectrometry-based detection analyzes cells with binding reagents that are "mass tagged", i.e., tagged with an element or isotope having a defined mass, e.g. a high-atomic mass, non-biological element. In the methods of the invention, labeled particles are introduced into a detector, e.g. a mass cytometer, atomic mass spectrometer (ICP-MS), etc., where they are atomized and ionized. The particles or solution are then subjected to elemental analysis, which identifies and measures the abundance of the mass tags used. The identities and the amounts of the isotopic elements associated with each particle or solution sample are then stored and analyzed.

The present invention allows for extremely sensitive highly multiplexed applications, where a large number of elemental tags are used in simultaneous or sequential detection and measurement of biologically active material. Multiplex applications may analyze more than about 10, more than about 15, more than about 20, more than about 25, more than about 30, more than about 40, more than about 50 different probes.

Analysis of cells is of particular interest, where the probes may bind to the cell surface, or to cytoplasmic and nuclear components of permeabilized cells. Alternatively bead and solution based assays are performed. In some embodiments the components of signaling pathways are analyzed, e.g. for changes in post-translational modification of proteins, such as phosphorylation and the like. Other embodiments include imaging applications where the detector is a LA-ICPMS (LA-laser ablation), where the laser scans a sample stained with elemental isotope reporters Compositions and methods are provided for the use of nanoparticles, which may be referred to herein as mass dots, as mass tags for probes such as antibodies, aptamers, nucleic acids, etc. in multiplexed bioassays with ICP-MS detection. A probe may be conjugated to one or more mass dots; usually not more than about 10 mass dots are conjugated to a single probe. In a preferred embodiment, the mass dots are comprised of substantially pure isotope preparations, e.g. at least about 90%, at least about 95%, at least about 99%, at least about 99.9%, at least about 99.99%, at least about 99.999%, at least about 99.9999% purity or more. Preferably the mass dot is free of high atomic mass dopants, as such dopants can occupy otherwise useful channels of instrument detection that could be used to detect other species of tagging isotope. Alternatively, when contamination by additional high atomic mass elements is unavoidable, the sum of atoms of all of the tagging isotopes in a composite isotope tag may be calculated during elemental analysis, and correlated with the abundance of the mass dot. In a third scenario, two or more isotopes or elements may be combined in a single reagent at a known stoichiometric ratio and total abundance for the purpose of multiplexing beyond the limit of discrete analysis channels on the instrument, with the identity and abundance of each tag being determined by subsequent deconvolution of the composite signal by Fourier transformation.

Mass dots are generally of a size large enough to enable highly sensitive detection of very small quantities of analyte, e.g. comprising at least about 500 metal atoms, at least about $10^3$ metal atoms, at least about $2.5 \times 10^3$ metal atoms, at least about $5 \times 10^3$ metal atoms, at least about $7.5 \times 10^3$ metal atoms, at least about $10^4$ metal atoms, and not more than about $10^5$ metal atoms. The size may vary with the specific isotope and chemical formulation, including surface coatings. The use of a dot of this size increases the sensitivity of ICP-MS-based assays over conventional chelation methods by 10- or 100-fold. Solid metal nanoparticles can be attached to biomolecules at a single linkage site, thereby minimizing the detrimental effects of protein denaturation which is required to attach multiple chelators per molecule of detection reagent. The mass dots in the present invention may be optimized to contain the highest concentration per unit volume of the desired high-mass metal atom of a particular isotopic mass. Counter-anions with small atomic radii and low masses may be used preferentially, for example fluorine, in the formulation of nanocrystal cores. Alternatively, counter-anions may be selected that provide useful functions, such as modification of solubility, hydrophobicity, hydrophilicity, electrical conductance, magnetic, paramagnetic or supermagnetic qualities, electrical conducting or superconducting qualities.

In some embodiments the mass dots are doped with organic or amphipathic molecules (e.g. chitosan, oleic acid) to increase hydrophilicity, or to decorate the surface with moieties that are amenable to further chemistry (e.g. carboxylic acids, sulfhydryls, amines, aldehydes, esters, aromatic hydrazides, aromatic aldehydes, hydroxides, etc.). These types of derivatization moieties may be incorporated into mass dots by many methods, including co-crystallization, surface chemistry, or polymer coating. Once incorporated, these moieties can be functionalized using reagents such as hetero-bifunctional cross linkers to facilitate covalent conjugation to detection reagents such as antibodies.

In other embodiments the mass dot is coated with a silica or siloxane coating, optionally functionalized with thiol, amine, carboxyl, aromatic hydrazide, or aromatic aldehyde groups. Silica is a convenient material for coating metal nanoparticles due to the ability to form a stable shell around the particle and the relative non-reactivity of silica in biological environments.

In other embodiments the mass dot is coated with an amphipathic polymer coating. The hydrophobic portion of the amphipathic polymer facilitates binding of the coating to the hydrophobic metal core, while the hydrophilic portion limits non-specific binding with biological substrates.

In some embodiments of the invention, a composition of probe conjugated to a mass dot as described herein is provided, where the probe may be dry, or provided in a suitable excipient. In some embodiments a plurality of such probes are provided, e.g. as a kit for detection of a cellular phenotype of interest, e.g. a panel of cancer-associated antigens; a panel of epitopes; a panel of reagents selective for a signaling pathway of interest, a panel of pathogen antigens or antibodies specific for pathogen antigens, and the like. Alternatively a kit may comprise a plurality of mass dots suitable for conjugation, with such reagents as are require for conjugating to probes of interest. Kits may also comprise buffers, controls, instructions for use, and the like.

In other embodiments of the invention, a DADS: Daughter Assayable Detector Species is utilized for labeling, where the DADS may be a metal encoded nano-object (MENOS), as described above, or may be a structural unit encoded nano-object (SUENOS), which is a unique molecular weight organic molecule that is detected in mass spectrometry as a distinct species. Various linkages are useful in attached a DADS to the particle for analysis, including without limitation covalent linkage, affinity linkage such as a DNA or protein ligand, etc.

Other features and advantages of the present invention will become apparent from the following detailed description. It should be understood, however, that the detailed description and the specific preferred embodiments of the invention are given by way of illustration only, since various changes and modifications within the spirit and scope of the invention will become apparent to those skilled in the art from this detailed description.

DEFINITIONS

Figure 1:
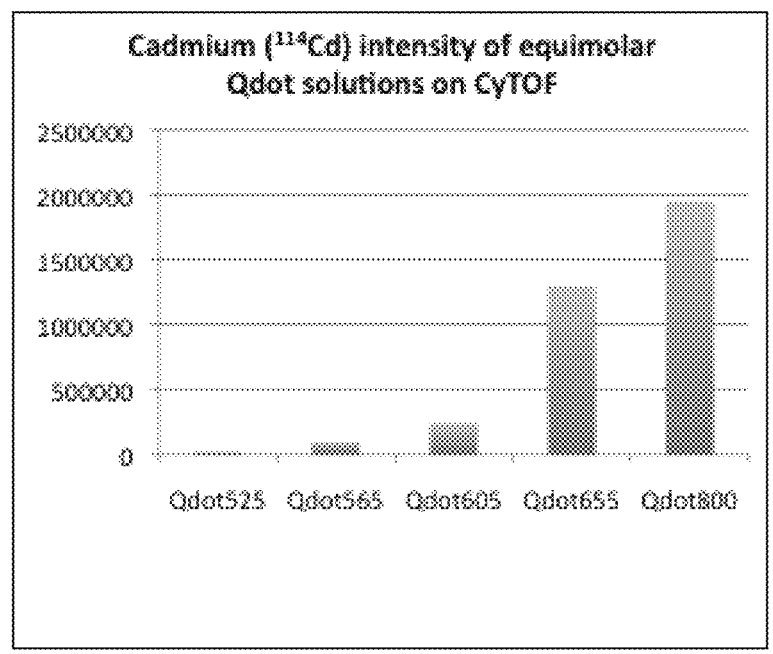
FIG. 1. Equimolar solutions of quantum dots of increasing size (indicated by increasing emission wavelength—bottom) were measured by ICP-MS (FIG. 1). As expected, increasing particle size lead to a proportional increase in Cd signal (Intensity counts per second) as reported by the $Cd^{114}$ measurement, Cd's most abundant naturally occurring isotope—summarized in the bar graph. Units are counts per minute.
Figure 1:
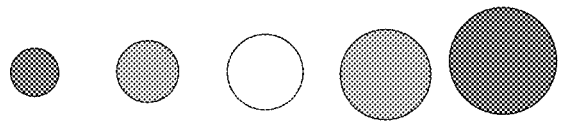

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Mass dots. Mass dots are nanoparticles of a high-atomic mass, non-biological element. Mass dots are of a size large enough to enable highly sensitive detection of very small quantities of analyte by ICP-MS, e.g. comprising at least about 500 metal atoms, at least about $10^3$ metal atoms, at least about $2.5 \times 10^3$ metal atoms, at least about $5 \times 10^3$ metal atoms, at least about $7.5 \times 10^3$ metal atoms, at least about $10^4$ metal atoms, and not more than about $10^5$ metal atoms. Mass dots may alternatively be 2+ elements in defined stochoimetric ratios for multiplexing, or due to impurities. Preferred counter-anions are of a molecular weight outside the sensitive detection range of the ICP-MS instrument, and have a small atomic radius, which provides for a higher number of metal atoms per unit of space than counter-anions with a larger atomic radius. Elements of interest include, without limitation, the lanthanide series of the periodic table, which comprises 15 elements, 14 of which have stable isotopes (La, Ce, Pr, Nd, Sm, Eu, Gd, Tb, Dy, Ho, Er, Tm, Yb, Lu), and are useful as tagging isotopes due to their rarity in the biosphere. In other embodiments, tagging isotopes comprise non-lanthanide elements that can form stable nanoparticles or nanocrystals for the applications described herein. These may include the high molecular weight members of the transition metal (e.g. Rh, Ir, Cd, Au, Ag, Pd, Hf, In), post-transition metals (e.g. In, Sb, Sn, Pb), metalloids (e.g. Te, Bi), alkaline metals, halogens, or actinides. In some embodiments, tagging isotopes may comprise radioactive elements that can form nanoparticles for the applications described herein (e.g. $^{131}$I). In other embodiments, tagging isotopes comprise any metal isotope not present in the biological analyte under study, ideally in the mass range of 100-240 A.M.U.

Mass dots are generally comprised of substantially pure isotope preparations, e.g. at least about 90%, at least about 95%, at least about 99%, at least about 99.9%, at least about 99.99%, at least about 99.999%, at least about 99.9999% purity or more. Preferably the mass dot is free of high atomic mass dopants.

In alternative embodiments, mass dots contain a defined mixture of a plurality of high-mass elements or isotopes. For example, mass dots may contain a 1:2 molar ratio of $^{169}$Tm and $^{159}$Tb. Objectives of using a defined mixture of high-mass elements or isotopes may include increasing the molar ratio of high-mass elements to low-mass elements, conferring stability to nanoparticles, achieving desired crystal geometries, or avoiding the expense of eliminating natural impurities. In some embodiments, the composite nanoparticles are synthesized such that the total abundance of each element is restricted to a narrow range, allowing multiplexing of reagents beyond the number of discrete analysis channels on the instrument. In some embodiments, mass dots may contain a plurality of high mass elements in the nanoparticle core (e.g. EuTe nanocrystals), serving as a composite isotope tag.

Multiple metals at known ratios and abundances can be used for multiplexing. This is a desirable feature of nanoparticles because they can be constructed and characterized within very tight tolerances. By contrast, solution-based methods are subject to stochasticity and mass action, so each reagent preparation will have a range of labeling intensities per molecule.

Although not required, in some embodiments, the nanoparticles are nanocrystals. Nanocrystals may be formed by de novo crystallization of an ionic solution, or by micronization of a larger crystalline solid. It is recognized that ionic interactions with other elements are required to form a crystal lattice. It is desirable that the nanocrystal lattices be compact, containing a high density of tag atoms, e.g. at least about 20, at least about 25, at least about or more 30 tag atoms/nm$^3$, and containing only elements that will neither interfere with the signal from other isotope tags, nor with the detection method itself. For example, lanthanide elements form stable nanocrystals with a high density of tag atoms per unit volume, e.g. lanthanum trifluoride (LaF$_3$) forms compact, water insoluble nanocrystals with a high density of lanthanum atoms. Exemplary synthetic methods are provided in the Examples.

Crystal structures contain counter-anions that may also be detected by an elemental analysis platform such as ICP-MS. In some embodiments of the present invention, nanocrystals may be synthesized using a single high-mass element as the tagging isotope, and one or more low-mass elements as counter-anions. An objective of using low-mass elements as counter-anions is to limit the amount of signal on detection channels that would be useful for multiplexed analysis of high-mass isotope tags. Counter-anions with small atomic radii and low masses may be used preferentially in the formulation of nanocrystal cores. Alternatively, counter-anions are selected that provide useful functions, such as modifying solubility hydrophobicity, hydrophilicity, electrical conductance, magnetic or supermagnetic qualities, electrical conducting or superconducting qualities.

In some embodiments the mass dots are doped with organic or amphipathic molecules (e.g. chitosan, oleic acid) to increase hydrophilicity, or to decorate the surface with moieties that are amenable to further chemistry (e.g. carboxylic acids, sulfhydryls, amines, aldehydes, esters, hydroxides, aromatic hydrazides, aromatic aldehydes, etc.). These types of derivatization moieties may be incorporated into mass dots by many methods, including co-crystallization, surface chemistry, or polymer coating. The number of derivatization moieties per mass dot may be tightly controlled to limit the number of detection reagent molecules that may be conjugated per mass dot in a later step. Once incorporated, these moieties can be functionalized using reagents such as heterobifunctional cross linkers to facilitate covalent conjugation to detection reagents such as antibodies.

In other embodiments the mass dot is coated with a silica or siloxane coating, optionally functionalized with thiol, amine, carboxyl, aromatic hydrazide, or aromatic aldehyde groups. The number of functional groups per mass dot may be tightly controlled to limit the number of detection reagent molecules that may be conjugated per mass dot in a later step. Silica is a convenient material for coating metal nanoparticles due to the ability to form a stable shell around the particle and the relative non-reactivity of silica in biological environments.

In other embodiments the mass dot is coated with an amphipathic polymer coating. The hydrophobic portion of the amphipathic polymer facilitates binding of the coating to the hydrophobic metal core, while the hydrophilic portion limits non-specific binding with biological substrates.

The nanoparticle core of the mass dot may have a defined size range, which may be substantially homogeneous, where the variability may be not more than 100% of the diameter, not more 50%, not more than 10%, etc.

Probes.

As used here, the term "probe" refers to a specific binding partner for an analyte of interest, where the probe is generally conjugated to one or more mass dots as described above. In some embodiments a single mass dot is conjugated to a probe. In other embodiments 2, 3, 4, 5, 6, 7, 8, 9, 10 or more mass dots are conjugated, usually not more than 10, and more usually not more than 5 mass dots are conjugated.

MENOs: Metal Encoded Nano-Objects. Nanoscale size particles with defined ratios of 1 or more isotopes. Each nanoparticle's signature ratio is distinct such that it would act as a unique DADS when bound to an BR. To use MENOs, one would create 100s, or 1000s of MENOs with unique signatures. These would be attached to BRs. The entire set of MENOs from a given cell are assayed individually in a manner that allows the cumulative number of given MENOs with a given ratio of elements to be determined on a per cell basis.

SUENOs: Structural Unit Encoded Nano-Objects (FIGS. 1B & C). A A SUENO can be: a) a small molecule of a defined molecular weight unique from other SUENOs. b) A polymeric substance of a defined molecular weight unique from other SUENOs. c) A small molecule of a defined molecular weight, or whose derived ions generated during mass spectrometry are uniquely generated or have unique masses and/or charges unique from other SUENOs. d) A polymer of distinct subunits that together have a defined molecular weight, or whose derived (i.e. by collision induced dissociation—CID) ions generated during mass spectrometry are uniquely generated or have unique masses and/or charges unique from other SUENOs.

Linkage between the mass dot, MENOS or SUENOS may be to a covalent, ionic, and/or amphipathic coating, preferably functionalized with a low molecular weight dopant, using any suitable linker. Illustrative entities include: Trioctylphosphine oxide, mercaptopropyltris(methyloxy)silane, aminopropyltris(methyloxy)silane, tetramethylammonium hydroxide, tetramethylammonium hydroxide pentahydrate, (trihydroxysilyl)propyl methylphosphonate, chlorotrimethylsilane, mercaptopropionic acid, 4-(dimethylamino)pridine, 5,5'-dithiobis(2-nitrobenzoic acid), azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC). Chemical groups that find use as couplings of Q to X include amide (amine plus carboxylic acid), ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), hydrazide (aromatic hydrazide plus aromatic aldehyde) and the like, as known in the art.

The term "specific binding member" as used herein refers to a member of a specific binding pair, i.e. two molecules, usually two different molecules, where one of the molecules through chemical or physical means specifically binds to the other molecule. The complementary members of a specific binding pair are sometimes referred to as a ligand and receptor; or receptor and counter-receptor. Specific binding indicates that the agent can distinguish a target antigen, or epitope within it, from other non-target antigens. It is specific in the sense that it can be used to detect a target antigen above background noise ("non-specific binding"). For example, a specific binding partner can detect a specific sequence or a topological conformation. A specific sequence can be a defined order of amino acids or a defined chemical moiety (e.g., where an antibody recognizes a phosphotyrosine or a particular carbohydrate configuration, etc.) which occurs in the target antigen. The term "antigen" is issued broadly, to indicate any agent which elicits an immune response in the body. An antigen can have one or more epitopes.

Binding pairs of interest include antigen and antibody specific binding pairs, complementary nucleic acids, peptide-MHC-antigen complexes and T cell receptor pairs, biotin and avidin or streptavidin; carbohydrates and lectins; complementary nucleotide sequences; peptide ligands and receptor; effector and receptor molecules; hormones and hormone binding protein; enzyme cofactors and enzymes; enzyme inhibitors and enzymes; and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies; and T cell antigen receptors, and their cognate MHC-peptide conjugates. Suitable antigens may be haptens, proteins, peptides, carbohydrates, etc. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

A nucleic acid based binding partner such as an oligonucleotide can be used to recognize and bind DNA or RNA based analytes. The term "polynucleotide" as used herein may refer to peptide nucleic acids, locked nucleic acids, modified nucleic acids, and the like as known in the art. The polynucleotide can be DNA, RNA, LNA or PNA, although it is not so limited. It can also be a combination of one or more of these elements and/or can comprise other nucleic acid mimics.

Binding partners can be primary or secondary. Primary binding partners are those bound to the analyte of interest. Secondary binding partners are those that bind to the primary binding partner.

Analytes.

As used herein, analytes refers to quantifiable components of cells or biological material, particularly components that can be accurately measured. An analyte can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. Some variability may be expected and a range of values may be obtained using standard statistical methods with a common statistical method used to provide single values.

Analytes of interest include cytoplasmic, cell surface or secreted biomolecules, frequently biopolymers, e.g. polypeptides, polysaccharides, polynucleotides, lipids, etc. In some embodiments, analytes include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric proteins. An analyte may be detection of a specifically modified protein or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one analyte while an inactive conformation of a receptor may comprise another, e.g. the active and inactive forms of heterodimeric integrin.

Analytes of interest include biological molecules in a variety of spatial configurations, on a variety of substrates, and in a variety of degraded states. An analyte may be a naturally occurring protein in its native conformation or chemically altered, denatured state. An analyte may be affixed to the cell in its native orientation, or it may be adhered to a variety of substrates, including synthetic substrates e.g. glass, plastic, or metal. An analyte may be affixed to planar substrates or bead-like substrates in a suspension. An analyte may be affixed to a substrate in a particular orientation by a second binding reagent, such as an antibody, as in the case of a sandwich ELISA.

Analytes of interest include polypeptides, and the epitope that is being quantitated by be a primary amino acid epitope, an epitope formed by protein secondary or tertiary structure, an epitope formed by two or more interacting polypeptides, or an epitope that results from posttranslational modification of a polypeptide.

Among the post-translational modifications that can be probed, are protein specific glycoslyation. Membrane associated carbohydrate is exclusively in the form of oligosaccharides covalently attached to proteins forming glycoproteins, and to a lesser extent covalently attached to lipid forming the glycolipids. Many proteins are modified at their N-termini following synthesis; in most cases the initiator methionine is hydrolyzed and an acetyl group is added to the new N-terminal amino acid. Post-translational methylation occurs at lysine residues in some proteins. Post-translational phosphorylation is one of the most common protein modifications that occurs in animal cells, often as a transient mechanism to regulate the biological activity of a protein. In animal cells serine, threonine and tyrosine are the amino acids subject to phosphorylation. Sulfate modification of proteins occurs at tyrosine residues such as in fibrinogen and in some secreted proteins. Prenylation refers to the addition of the 15 carbon farnesyl group or the 20 carbon geranylgeranyl group to acceptor proteins, both of which are isoprenoid compounds derived from the cholesterol biosynthetic pathway. Modifications of proteins that depend upon vitamin C as a cofactor include proline and lysine hydroxylations and carboxy terminal amidation. Vitamin K is a cofactor in the carboxylation of glutamic acid residues that results in the formation of a γ-carboxyglutamate (gamma-carboxyglutamate), referred to as a gla residue.

Cells.

Cells for use in the assays of the invention can be an organism, a single cell type derived from an organism, or can be a mixture of cell types. Included are naturally occurring cells and cell populations, genetically engineered cell lines, cells derived from transgenic animals, etc. Virtually any cell type and size can be accommodated. Suitable cells include bacterial, fungal, plant and animal cells. In one embodiment of the invention, the cells are mammalian cells, e.g. complex cell populations such as naturally occurring tissues, for example blood, liver, pancreas, neural tissue, bone marrow, skin, and the like. Some tissues may be disrupted into a monodisperse suspension. Alternatively, the cells may be a cultured population, e.g. a culture derived from a complex population, a culture derived from a single cell type where the cells have differentiated into multiple lineages, or where the cells are responding differentially to stimulus, and the like.

Cell types that can find use in the subject invention include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells, etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. The American Type Culture Collection (Manassas, Va.) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) *Journal of Cellular Biochemistry* Supplement 24:32-91). Included are different cell lines derived spontaneously, or selected for desired growth or response characteristics from an individual cell line; and may include multiple cell lines derived from a similar tumor type but from distinct patients or sites.

Cells may be non-adherent, e.g. blood cells including monocytes, T cells, B-cells; tumor cells, etc., or adherent cells, e.g. epithelial cells, endothelial cells, neural cells, etc. In order to profile adherent cells, they must be dissociated from the substrate that they are adhered to, and from other cells, in a manner that maintains their ability to recognize and bind to probe molecules.

Such cells can be acquired from an individual using, e.g., a draw, a lavage, a wash, surgical dissection etc., from a variety of tissues, e.g., blood, marrow, a solid tissue (e.g., a solid tumor), ascites, by a variety of techniques that are known in the art. Cells may be obtained from fixed or unfixed, fresh or frozen, whole or disaggregated samples. Disaggregation of tissue may occur either mechanically or enzymatically using known techniques.

Various methods and devices exist for pre-separating component parts of the sample. These methods include filters, centrifuges, chromatographs, and other well-known fluid separation methods; gross separation using columns, centrifuges, filters, separation by killing of unwanted cells, separation with fluorescence activated cell sorters, separation by directly or indirectly binding cells to a ligand immobilized on a physical support, such as panning techniques, separation by column immunoadsorption, and separation using magnetic immunobeads.

As used herein, the term "elemental analysis" refers to a method by which the presence and/or abundance of elements of a sample are evaluated. "Capacitively coupled plasma" (CCP) means a source of ionization in which a plasma is established by capacitive coupling of radiofrequency energy at atmospheric pressure or at a reduced pressure (typically between 1 and 500 Torr) in a graphite or quartz tube. The term "inductively coupled plasma" (ICP) means a source of atomization and ionization in which a plasma is established in an inert gas (usually argon) by the inductive coupling of radiofrequency energy. The frequency of excitation force is in the MHz range. The term "plasma source" means a source of atoms or atomic ions comprising a hot gas (usually argon) in which there are approximately equal numbers of electrons and ions, and in which the Debye length is small relative to the dimensions of the source. The term "flow cell" refers to a conduit in which particles flow, in a medium, one by one in single file. The term "a diverter" refers to a branch of a flow cell in which particles can be separated from other components passing through the flow cell. "Laser ablation" means a source of combusted material liberated from an otherwise intact surface by exposure to laser radiation, optionally used in conjunction with microscopy to preserve spatial information. "Mass spectrometer" means an instrument for producing ions in a gas and analyzing them according to their mass/charge ratio. "Microwave induced plasma" (MIP) means a source of atomization and ionization in which a plasma is established in an inert gas (typically nitrogen, argon or helium) by the coupling of microwave energy. The frequency of excitation force is in the GHz range. "Glow discharge" (GD) means a source of ionization in which a discharge is established in a low pressure gas (typically between 0.01 and 10 Torr), typically argon, nitrogen or air, by a direct current (or less commonly radiofrequency) potential between electrodes. "Graphite furnace" means a spectrometer system that includes a vaporization and atomization source comprised of a heated graphite tube. Spectroscopic detection of elements within the furnace may be performed by optical absorption or emission, or the sample may be transported from the furnace to a plasma source (e.g. inductively coupled plasma) for excitation and determination by optical or mass spectrometry.

Preferred methods for analysis of mass dots utilize ICP-MS. In some embodiments the ICP-MS is performed with solution analysis, for example ELAN DRC II, Perkin-Elmer. In other embodiments the analysis is performed with a mass cytometer (e.g. CyTOF, DVS Sciences), which uses a nebulizer to administer a suspension of cells, beads, or other particles in a single-particle stream to an ICP-MS chamber, thereby yielding single particle/cell data similar to a flow cytometer. Alternatively the analysis is performed by an elemental analysis-driven imaging system (e.g. laser ablation ICP-MS). Devices for such analytic methods are known in the art.

DETAILED DESCRIPTION OF THE EMBODIMENTS

Compositions and methods are provided for the sensitive detection of an analyte through specific binding to a probe labeled with a mass dot, i.e. a nanoparticle of a high-atomic mass, non-biological element of a size and uniformity sufficient to enable highly sensitive detection of very small quantities of analyte, and usually substantially pure isotope of the high-atomic mass element.

Analytes of interest include any molecule in which a specific binding partner can be devised and labeled with a mass dot, e.g. arrays of polynucleotides or proteins, histochemistry slides, ELISA plates, and the like. The methods of the invention find particular use in highly multiplexed applications, where multiple different probes are applied to a sample.

In one embodiment, the analyte is present on cells or beads in a single particle suspension. Examples of cells of interest are described above. If beads are employed, the beads can range in size from 20 nM to 200 μM or larger, and may be made of polystyrene, but other materials such as polymethylmethacrylate (PMMA), polyvinyltoluene (PVT), styrene/butadiene (S/B) copolymer, styrene/vinyltoluene (S/VT) can also used. Alternatively analytes may be bound to a solid substrate, e.g. glass, plastic, etc.

The analyte is contacted with the mass dot labeled probe, and incubated for a period of time sufficient to bind the available analyte. The incubation will usually be at least about 2 minutes and usually less than about 24 hours. It is desirable to have a sufficient concentration of probe in the reaction mixture so that the efficiency of detection is not limited by lack of probe. The appropriate concentration is determined by titration. Where the labeling is direct, the probe is labeled with a mass dot. Where the labeling is indirect, a second stage probe or label can be used, by washing and resuspending in medium prior to incubation with the second stage probes.

Where the analyte is present in or on cells, the cells may be labeled on the surface, or may be located in the cytoplasm or nucleus of the cell. For such intracellular labeling it is generally desirable to fix and permeabilize the cells. For example, where transient signaling pathways are being analyzed, it is desirable to fix the cells at the desired timepoint, then permeabilize to allow the probes access to the intracellular environment. Various fixatives are known in the art, including formaldehyde, paraformaldehyde, formaldehyde/acetone, methanol/acetone, etc. Paraformaldehyde used at a final concentration of about 1 to 2% has been found to be a good cross-linking fixative. Permeabilizing agents are known in the art, and include mild detergents, such as Triton X-100, NP-40, saponin, etc.; methanol, and the like. It may also be desirable to label cells with a positive heavy metal control, e.g. a DNA intercalator labeled with a heavy metal, e.g. iridium, etc. Cells may also be stained with a viability dye prior to fixation, e.g. ethidium bromide, $RhCl_3$, etc., as known in the art.

The analyte is washed of unbound probe using any suitable method known in the art. For example cells or beads may be pelleted and washed in PBS or normal saline; polynucleotide arrays, beads, blots and the like are washed with a buffer of suitable stringency; and the like as known in the art.

The labeled analyte is then analyzed by, for example, inductively coupled plasma mass spectrometry (ICP-MS) identity to determine the abundance of the mass tag for the particle or other element, methods for performance of which are readily adapted from known methods. In particular embodiments the mass dots are vaporized, atomized and ionized by plasma (e.g., inductively coupled plasma) to produce ions that are subsequently analyzed by a mass spectrometer or emission spectroscopy to provide the identity and/or determine the abundance of the mass dots. The data produced by the elemental analysis of the mass dots.

Where particles or cells are being analyzed, they may be analyzed on a mass cytometer, in which cells are introduced into a fluidic system and introduced into the mass cytometer one cell at a time. In one embodiment, cells are carried in a liquid suspension and sprayed into a plasma source by means of a nebulizer. In another embodiment, the cells may be hydrodynamically focused one cell at a time through a flow cell using a sheath fluid. In particular embodiments, the particle may be compartmentalized in the flow cell by introduction of an immiscible barrier, e.g., using a gas (e.g., air or nitrogen) or oil, such that the particle is physically separated from other particles that are passing through the flow cell. The particles may be compartmentalized prior to or during introduction of the particle into the flow cell by introducing an immiscible material (e.g., air or oil) into the flow path.

The general principles of mass cytometry, including methods by which single cell suspensions can be made, methods by which cells can be labeled using, e.g., mass-tagged antibodies, methods for atomizing particles and methods for performing elemental analysis on particles, as well as hardware that can be employed in mass cytometry, including flow cells, ionization chambers, reagents, mass spectrometers and computer control systems are known and are reviewed in a variety of publications including, but not limited to Bandura et al Analytical Chemistry 2009 81 6813-6822), Tanner et al (Pure Appl. Chem 2008 80: 2627-2641), U.S. Pat. Nos. 7,479,630 (Method and apparatus for flow cytometry linked with elemental analysis) and 7,135,296 (Elemental analysis of tagged biologically active materials); and published U.S. patent application 20080046194, for example, which publications are incorporated by reference herein for disclosure of those methods and hardware.

The results of such analysis may be compared to results obtained from reference compounds, concentration curves, controls, etc. The comparison of results is accomplished by the use of suitable deduction protocols, AI systems, statistical comparisons, etc.

In particular embodiments, the method described above may be employed in a multiplex assay in which a heterogeneous population of cells is labeled with a plurality of distinguishably mass dot labeled binding agents (e.g., a number of different antibodies). As there are more than 80 naturally occurring elements having more than 250 stable isotopes, the population of cells may be labeled using at least 5, at least 10, at least 20, at least 30, at least 50, or at least 100, up to 150 or more different binding agents (that bind to, for example different cell surface markers) that are each tagged with a different isotopically pure mass dot. After the population of cells is labeled, the cells are introduced into the flow cell, and individually analyzed using the method described above.

A database of analytic information can be compiled. These databases may include results from known cell types, references from the analysis of cells treated under particular conditions, and the like. A data matrix may be generated, where each point of the data matrix corresponds to a readout from a cell, where data for each cell may comprise readouts from multiple mass dot labels. The readout may be a mean, median or the variance or other statistically or mathematically derived value associated with the measurement. The output readout information may be further refined by direct comparison with the corresponding reference readout. The absolute values obtained for each output under identical conditions will display a variability that is inherent in live biological systems and also reflects individual cellular variability as well as the variability inherent between individuals.

Kits

Also provided by the present disclosure are kits for practicing the method as described above. The subject kit contains reagents for performing the method described above and in certain embodiments may contain a plurality of labeled specific binding reagents, wherein each of the labeled specific binding reagent specifically binds a different target and each of the mass dot tags are distinguishable from one another by elemental analysis. The kit may also contain a reference sample to which results obtained from a test sample may be compared.

In addition to above-mentioned components, the subject kit may further include instructions for using the components of the kit to practice the methods described herein. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to above-mentioned components, the subject kit may include software to perform comparison of data.

Utility

Exemplary analytic methods employing the above-described method include, for example, antigen identification, disease diagnostics, and the like, particularly methods in which high levels of sensitivity and multiplexing are required.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Quantitative Comparison of CyTOF and LSR2 Sensitivity to Qdot-Stained Cells

In order to assess the feasibility of applying nanoparticles to bioassays with atomic mass spectrometry detection we used commercially available quantum dots (QDots™) as a test material because they fall within the general physical requirements for mass dot applications. Non-isotopically-enriched Qdots were measured by summing the abundance of multiple cadmium isotopes, which are detected as distinct masses by the instrument. Quantum dots are nanocrystals primarily composed of the element cadmium doped with small amounts of the element tellurium. By controlling the amount of dopant and the size of the quantum dot the fluorescent properties can be modulated—where larger quantum dots generally have longer emission wavelengths. Cadmium contains 8 stable mass isotopes between the atomic masses of 106 and 116. While not ideal, the signal for these particles was measured by monitoring the 6 most abundant isotopes. Also of note, if isotopically pure Qdots were available, they could potentially add 8 additional mass channels for simultaneous quantification by atomic mass spectrometry in biological assays.

First, to assess efficiency of the ability to measure reporter elements from nanocrystals/nanoparticles, equimolar solutions of quantum dots of increasing size (hence increasing emission wavelength) were measured by ICP-MS (FIG. 1). As expected, increasing particle size lead to a proportional increase in Cd signal as measured by $Cd^{114}$, Cd's most abundant naturally occurring isotope. These results indicate that increasing number of atoms present in a solid nanoparticle, as predicted, will result in a proportion increase in measured reporter signal.

Figure 2:
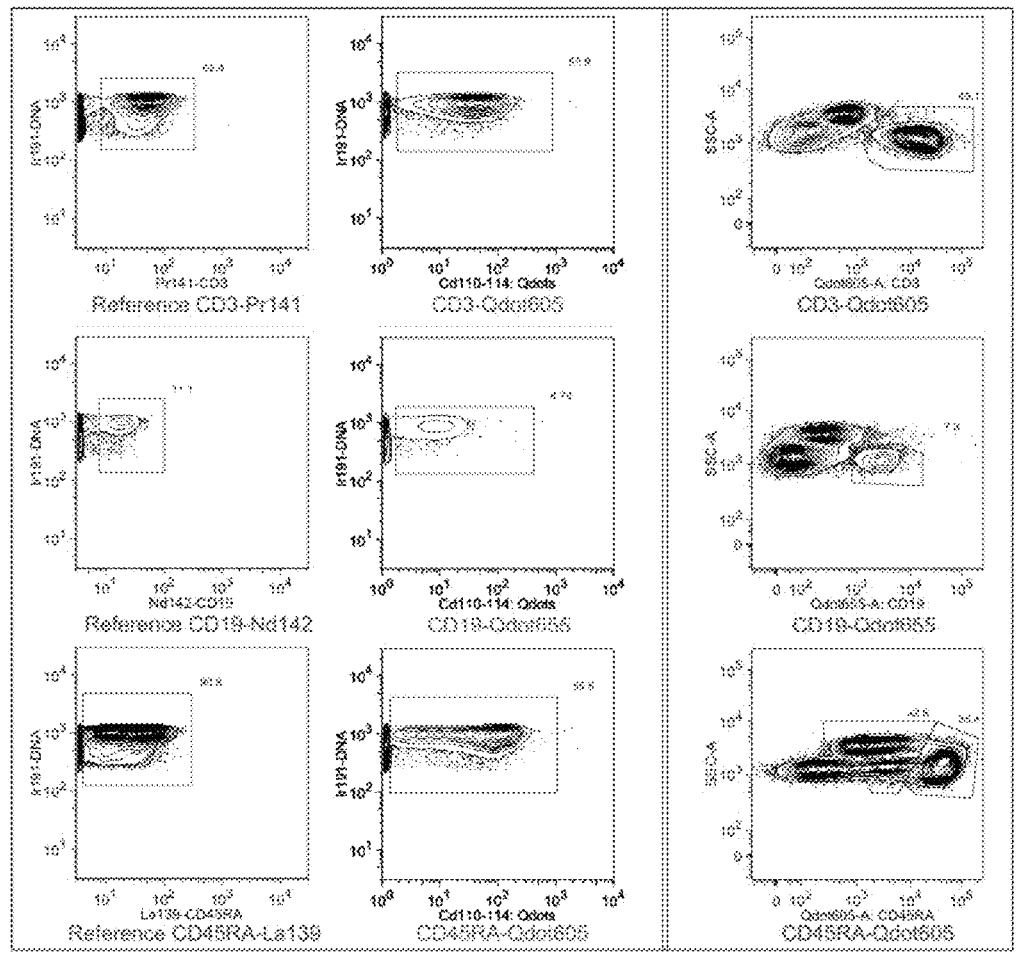
FIG. 2. Peripheral blood mononuclear cells (PBMCs) were stained with the indicated Invitrogen Qdot reagents, or the same antibody clones conjugated with traditional MaxPAR reagents and the indicated reported elemental isotope. The results of the MaxPAR and quantum dot staining as measured by mass cytometry are shown in the left and center columns, respectively. The same quantum dot labeled samples was then measured on the LSR-II collecting Qdot655 fluorescence, right column. Positive cell populations are indicated with the blue box and population frequency as a percentage of the whole samples is listed.
Figure 3:
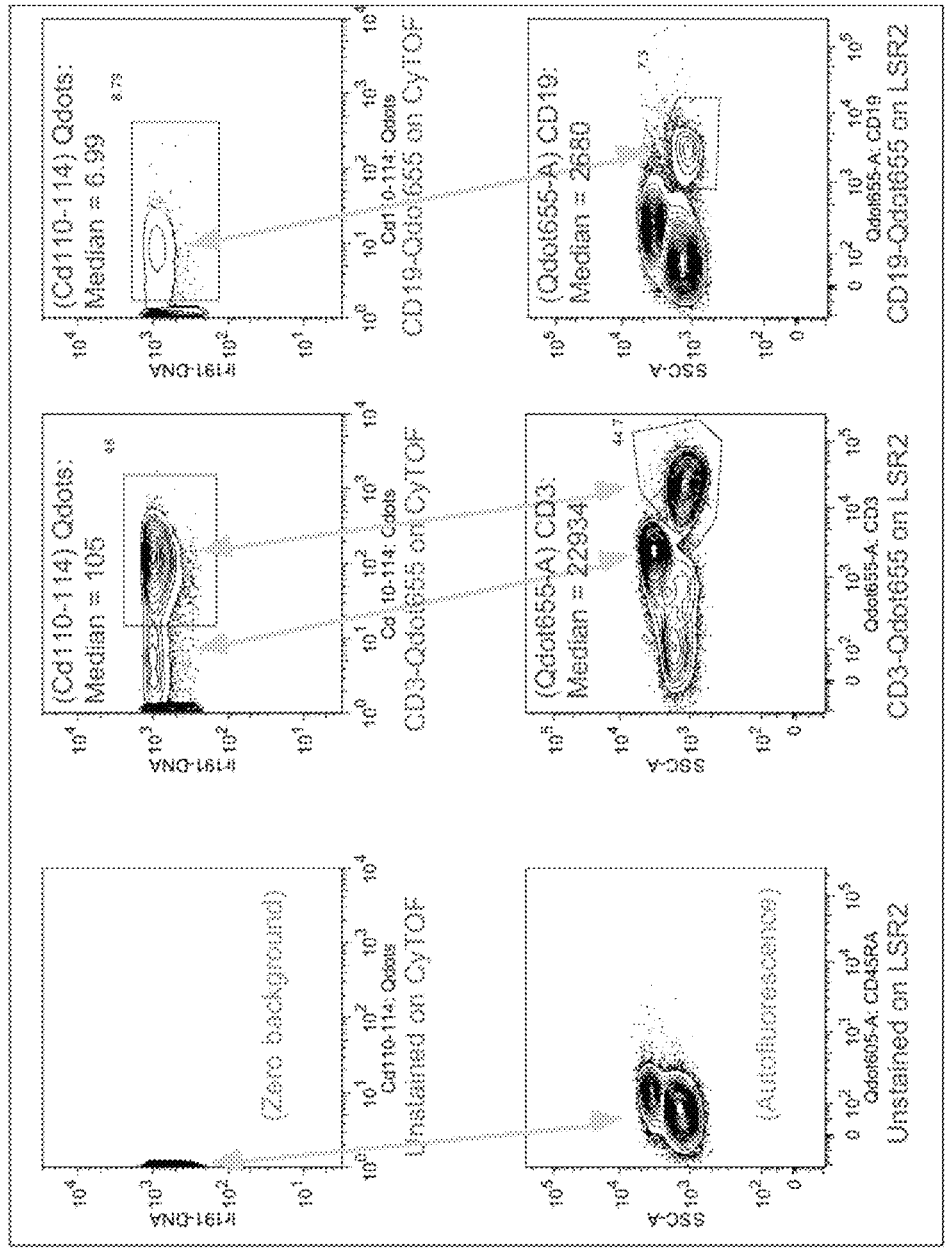
FIG. 3. Closer comparison of the CD19 and CD3 quantum dot results from PBMC staining as measured by mass cytometry (top) and fluorescence flow cytometry (bottom). The left contour plots show the difference in background signal on the two platforms as exemplified by analysis of unstained PBMC samples. It is this lack of background signal in the mass cytometry analysis with contributes to the enhanced measurement resolution. The center and right contour plots show the results of CD3 and CD19 staining on the same PBMC samples. The median intensity of the positive cell population (blue box) as measured by atomic mass spectrometry or fluorescence is shown. CD3 is 15 fold stronger than CD19 by mass cytometry where CD3 is only 8.5 fold brighter of LSR-II using the same Qdot 655. Overall, this indicates at least a 76% improvement of sample resolution between different cell populations by mass cytometry using the same reagent.

To assess the utility of these particles in bioassays, single cell analysis was performed on samples stained with nanoparticle reagents (Quantum Dots, Invitrogen) in comparison to conventional elemental reporter labeling reagents (MaxPAR, DVS sciences) as measured by a single cell CyTOF™ mass cytometer (FIG. 2). The same samples stained with the quantum dot reagents were then measured by traditional fluorescence flow cytometry to confirm the accuracy of measurement and compare the fluorescence and atomic mass spectrometry detection platforms (FIG. 2-3). Here, peripheral blood mononuclear cells (PBMCs) were stained with the indicated QDot reagents, or the same antibody clones conjugated with traditional MaxPAR reagents and the indicated reported elemental isotope. For the quantum dot reagents the same tube was first run on CyTOF (collecting cadmium ion abundance across the 6 most abundant isotopes), then on the LSR-II (collecting Qdot655 fluorescence) (FIG. 2-3).

Quantum dot measurements by mass cytometry revealed similar cell frequencies and a higher overall signal compared to conventional mass cytometry reagents (FIG. 2 left and center). The fact that the quantum dot reagents already yield a higher single-cell signal as compared to conventional mass cytometry (MaxPAR) reagents is promising as Cd falls into the range of lower sensitivity, as compared to the Lanthanide metals used in the MaxPAR reagents. Additionally, the Cd signal here is split between 8 analysis channels, requiring 8, as opposed to 1, atomic mass spectrometry limits of detection to be overcome. Again, as high MW elements of a purely monoisotopic nature are utilized we expect the benefits of the mass dot technology to become evermore apparent. Further to this, the accuracy of mass dot analysis by mass cytometry was confirmed by the similar frequencies observed through fluorescence analysis of the same samples by LSR-II fluorescence flow cytometry (FIG. 2-*left*).

Finally, quantitative comparison of the mass cytometry and fluorescence values for the same samples (FIG. 3) revealed that, when the mass cytometry measurements are on-scale, mass dot analysis as measure on the CyTOF has 76% better resolution between positive and negative cell populations compared to the same analysis by fluorescence. (CD3 is 15 fold stronger than CD19 on the CyTOF using the Cd channels to measure Qdot 655; CD3 is only 8.5 fold brighter of LSR-II using Qdot 655).

Collectively, these examples demonstrate Mass Dot feasibility, utility, as well as their potential improvement over existing technologies as a reporter in single cell analysis and other bioassays.

Example 2

Preparation of 20 nm-Diameter, Chitosan-Impregnated $EuF_3$ Nanocrystals

Combine:

| Volume | Concentration | Compound | Source |
|---|---|---|---|
| 10 ml | 0.2M | $^{151}EuCl_3$ | 98% enriched isotope Sigma |
| 25 ml | 1% w/v (in 0.05M HCl) | Chitosan, highly viscous | Fluka |
| 10 ml | 0.12 mols (0.2222 g in 10 mL water) | $NH_4F$ | Sigma |

Titrate pH to 6.5 with dilute ammonia. React 2 hrs at 75*C. Nanocrystals will form spontaneously. Centrifuge to purify nanocrystals. Wash multiple times with deionized water with 0.5% v/v acetic acid. Nanocrystals can be stored in deionized water at this point. In 1 ml of phosphate buffered saline (PBS) react 1 mg of antibody with 0.4 mg of N-(3-dimethylaminopropyl)-N-ethylcarbodiimide hydrochloride (EDAC) and 0.6 mg N-hydroxysuccinimide (NHS) to conjugate. After 15 min add 4 mg of nanocrystals and react for 2 hrs at ambient temperature. Quench reaction by adding 0.2 mL of 1M glycine pH 8. Wash several times in PBS.

Example 3

Preparation of 8 nm-Diameter, Oleic Acid-Impregnated $LaF_3$ Nanocrystals

Combine:

| Volume | Concentration | Compound | Source |
|---|---|---|---|
| 1 ml | 0.5M | $^{139}La(NO_3)_3$ | Sigma |
| 2 ml | 1.0M | NaF | Sigma |
| 20 ml | 100% | Ethanol | Sigma |
| 1.2 ml | 100% | Deionized water | Fisher |
| 10 ml | 100% | Oleic Acid | Sigma |

Stir the solution thoroughly until it becomes milky colloidal. Transfer it to a 50 mL Teflon lined autoclave and heat at 190*C for 6 h. Allow cooling to room temperature and collect the final product by means of centrifugation. Wash multiple times with ethanol to remove any possible remnants, and then dispersed in cyclohexane. At this point nano crystals could be functionalized with a photoreactive cross-linker. Alternatively, the carboxylic acid in the nanocrystal embedded oleic acid is reduced to an alcohol for further functionalized through treatment with a compound such as LiAlH under anhydrous conditions.

Example 4

Alternative Antibody Cross-Linking for Chitosan-Impregnated Nanocrystals

Synthesize nanocraystals according to Example 2 protocol, steps 1 through 5. Resuspend 2 mg of chitosan-impregnated nanocrystals (as in Example I) in 0.3 mL of 0.1M phosphate, pH 7.0. Add 16 mg (approximately 100-fold molar excess) of 4-(N-Maleimidomethyl)cyclohexanecarboxylic acid N-hydroxysuccinimide ester (Sigma) dissolved in 20 ul of N,Ndimethylformamide (DMF). Incubate for 1 hr stirring continuously at 30 degrees Celsius. Remove any precipitated by low speed centrifugation. Remove any free succinimide ester linker by gel filtration using a PD-10 column (Pharmacia) with a 0.1M phosphate buffer, pH 6.0. Concentrate the nanocrystal-containing fraction via centrifugal filtration. Lyophilize for long-term storage. In 0.1M sodium phosphate buffer, pH 6.5 with 5 mM (EDTA), combine a pre-reduced antibody preparation with maleimide-containing nanocrystals in a 1:1 ratio by weight. Incubate for 1 hr at 37 degrees Celsius. Purify the antibody/nanocrystal conjugate using size exclusion chromatography or differential ultracentrifugation.

Example 5

Nanoparticle Synthesis by Evaporative Condensation

To synthesize nanoparticles of $LaF_3$ and other RE fluorides of about 50 nm diameter.

We selected two approaches to produce nanoparticles of this material. One is based on evaporation condensation, and the other in the synthesis in the gas phase using a variation of the atmospheric pressure CVD using organometallic precursors. This report describes the work using evaporation condensation process.

Powders of LaF3 of high purity were loaded in a high purity graphite crucible with polished walls. The loaded crucible was thermally insulated using a layer of graphite felt and placed on a ceramic pedestal in a gas tight water cooled quartz jacket. Argon gas can be flown pass the crucible and injected through the top of the quartz jacket. The system was heated by direct induction provided by external coils powered by a Westinghouse 450 KHz Radio Frequency power supply. The temperature was measured by an Ircon dual wave length pyrometer.

The system was heated to temperatures above 1500° C. to melt the $LaF_3$ and obtain vapor pressures in the tens of millitorr range. The hot molecules of $LaF_3$ in the gas phase emerge from the crucible to find a much cooler region. Assuming that the vapor pressure inside the crucible was near the equilibrium value, as the gas molecules cool down the equivalent equilibrium pressure will drop by several orders of magnitude and a degree of supersaturation will occur and, the molecules will have a tendency to condense to form droplets (above 1440° C.) and solids below that temperature. Using the Kelvin equation we can get an approximate idea of the diameter of the droplets/powders formed:

$$Dp = 4 * \text{Surf Tension} \cdot \text{molec volume}/kBT \, Ln(\text{Saturation Ratio})$$

The diameter of the first to form particles, and the rate of nucleation are heavily dependent on the saturation ratio and on the surface energy of the species. Note that at the initial stages of condensation, the supersaturation has to be significantly high to compensate for the tendency of small (Angstrom radius) droplets to evaporate. As the cooling progresses, already formed particles will collide with each other and form agglomerates. By the time that the supersaturation is over 3 times, the condensation will expedite. It is expected that significant formation can happen while the $LaF_3$ is liquid and very fast nucleation will happen after it solidifies.

The incoming Ar gas is significantly cooler that the effluent vapors and the wall of the reactor are kept close to room temperature. Once formed, the nuclei grow by agglomeration (the rate of agglomeration is proportional to the concentration of nuclei to the square as in bimolecular collision theory) and then the agglomerates are propelled to the cool walls by thermophoretic forces, where they form a porous coating of independent particles.

Figure 4:
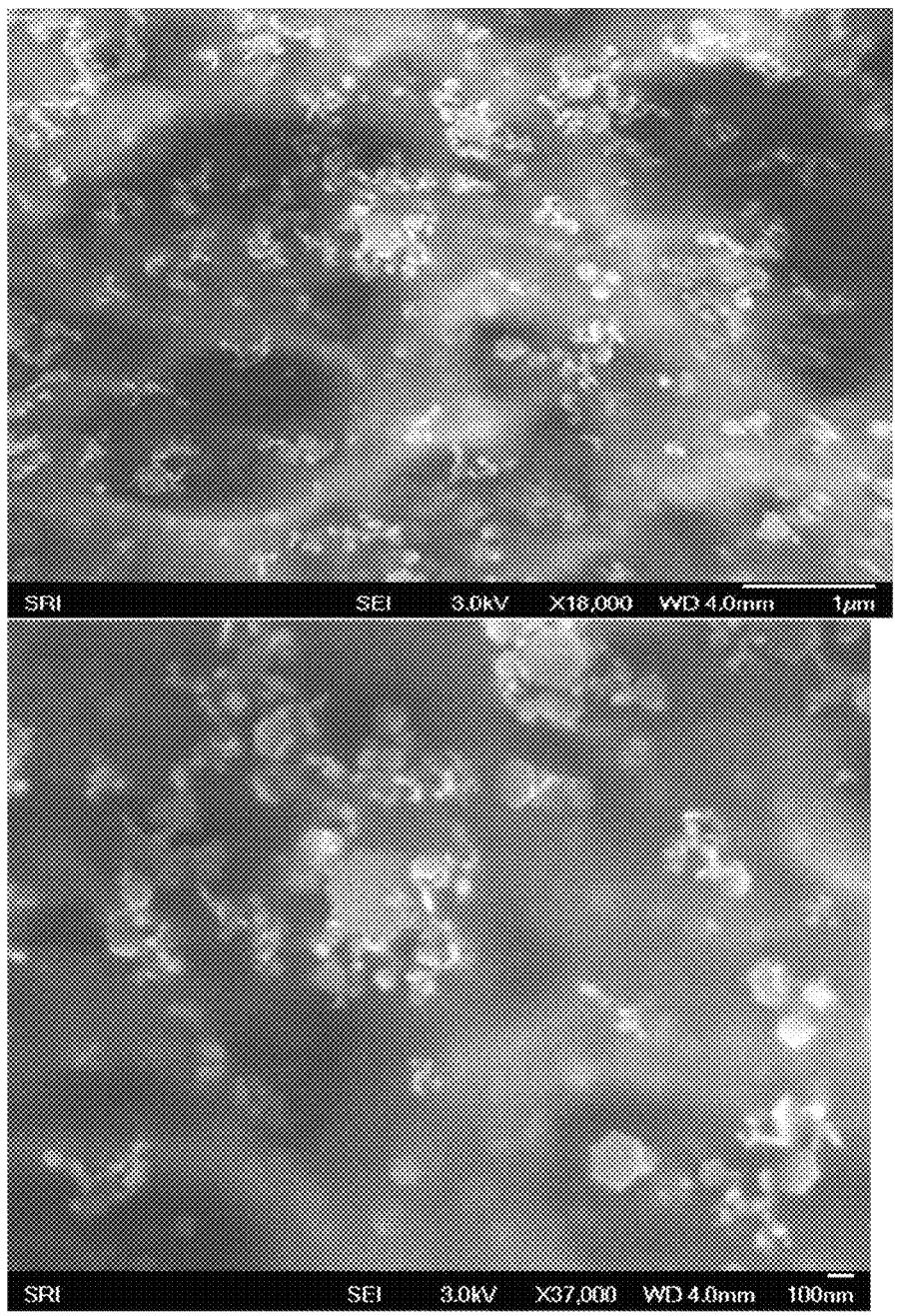
FIG. 4. Scanning electron micrograph of $LaF_3$ nanoparticles synthesized in a high-temperature ICP reactor through evaporation and subsequent condensation.

The particles were collected by washing the walls of the reactor with alcohol and kept in dispersion in a glass vial. Samples were taken by drying a droplet on a graphite substrate and analyzing the resulting particles by SEM. Examples of these particles are shown in FIG. 4.

Example 6

$PrF_3$ Nanoparticle Synthesis by Chemical Vapor Generation in a Fluidized Bed Reactor (CVG-FBR)

Figure 5:
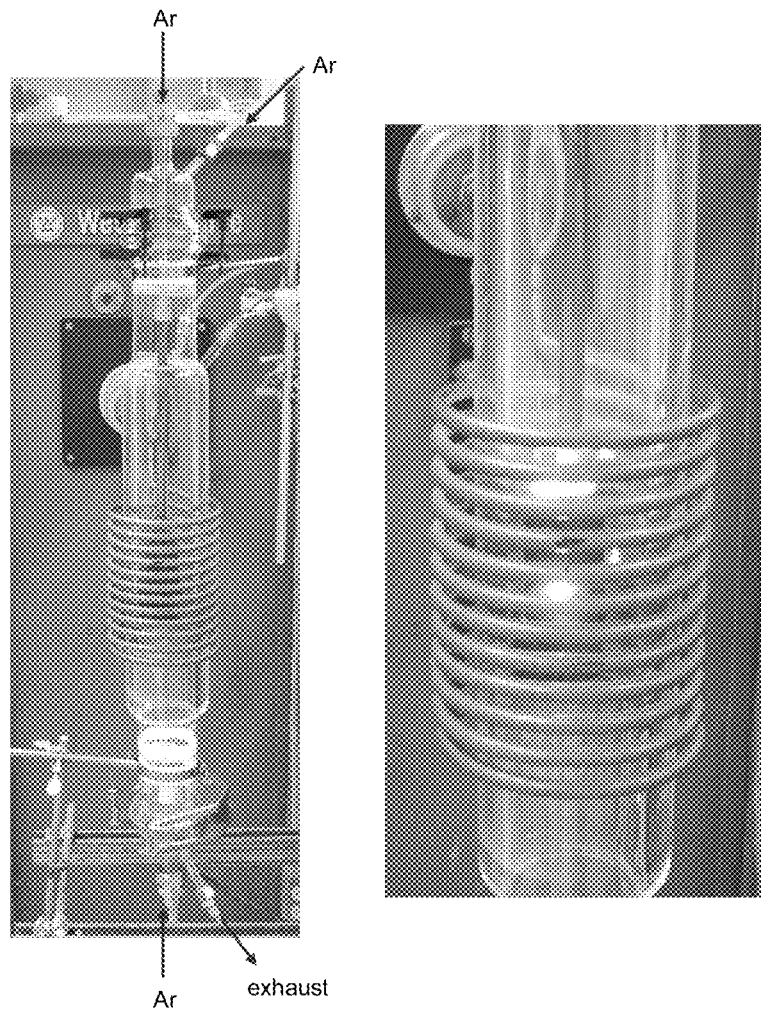
FIG. 5: Left: general view of reactor; Right: closer view at target temperature.

Powders of $PrF_3$ of high purity were loaded in a high purity graphite crucible with polished walls. The loaded crucible (18 mm ID, 30 mm OD, h=70 mm) was thermally insulated using a layer of graphite felt (total OD=40 mm) and placed on a porous graphite pedestal in a gas tight water cooled quartz jacket (72 mm ID) as shown in FIG. 5. Argon gas can be flown pass the crucible and injected through the top of the quartz jacket. The system was heated by direct induction provided by external coils powered by a Westinghouse 450 KHz radio frequency power supply. The temperature was measured at the crucible wall (close to the base, through an orifice in the felt insulator) by means of a dual wave length pyrometer.

Ar gas was fed through different ports in the reactor: 1000 sccm were supplied from the top directly into the main reactor space; 1100 sccm were fed through the graphite center tube, which had the open end at the same height as the top part of the crucible; finally, 350 sccm were fed through the tube holding the pedestal, which had lateral openings at its wide section (funnel-like zone). The system was heated at 1580° C. for one hour. This temperature is above the melting point of $PrF_3$ and the expected vapor pressure is of the order of several Torr.

Figure 6:
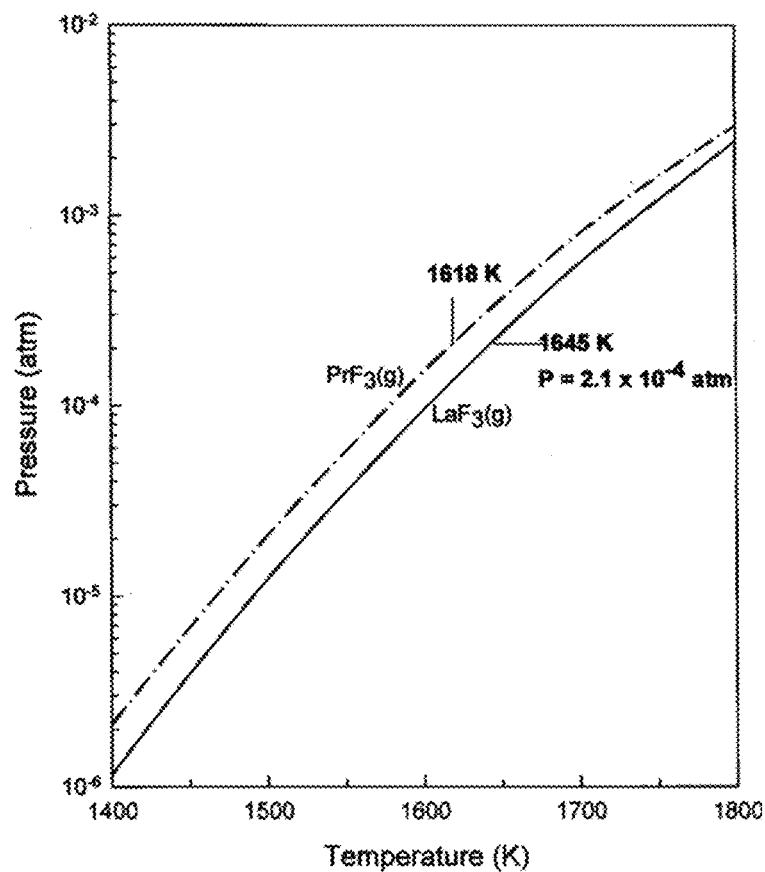
FIG. 6: Plot of vapor pressure vs temperature for $PrF_3(s)=PrF_3(g)$.

As explained in Example 5 for the synthesis of $LaF_3$ nanoparticles, the hot molecules of $PrF_3$ in the gas phase emerge from the crucible to find a much cooler region, where supersaturation occurs and the molecules have a tendency to form droplets or, below the melting point, solids (FIG. 6). In our reactor, the incoming Ar gas is significantly cooler that the effluent vapors and the wall of the reactor are kept close to room temperature. The nuclei grow by agglomeration and then are propelled to the cool walls by thermophoretic forces, where they form a porous coating of independent particles. The particles were scraped from the walls and dispersed in isopropyl alcohol.

Figure 7:
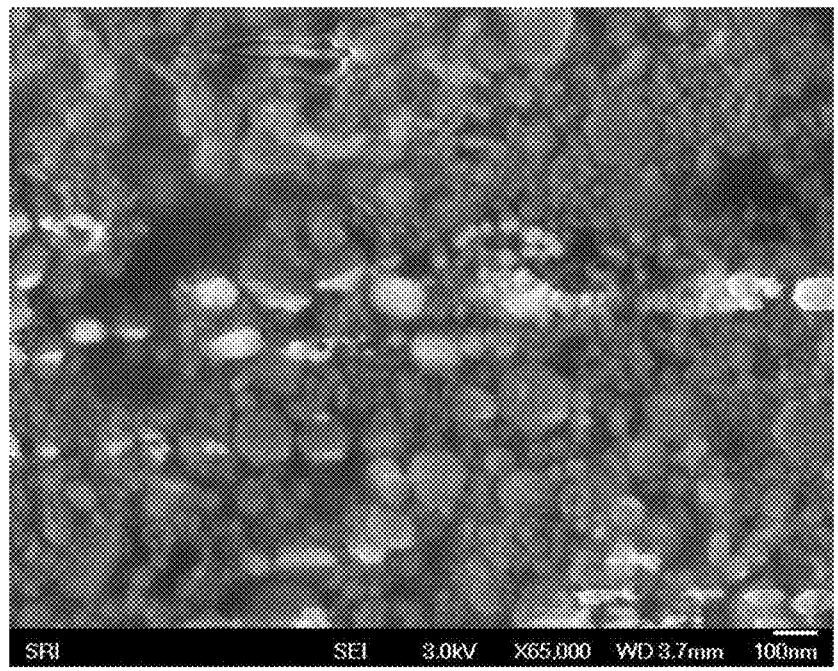
FIG. 7: SEM micrographs of PrF3 particles as collected from the walls.
Figure 8:
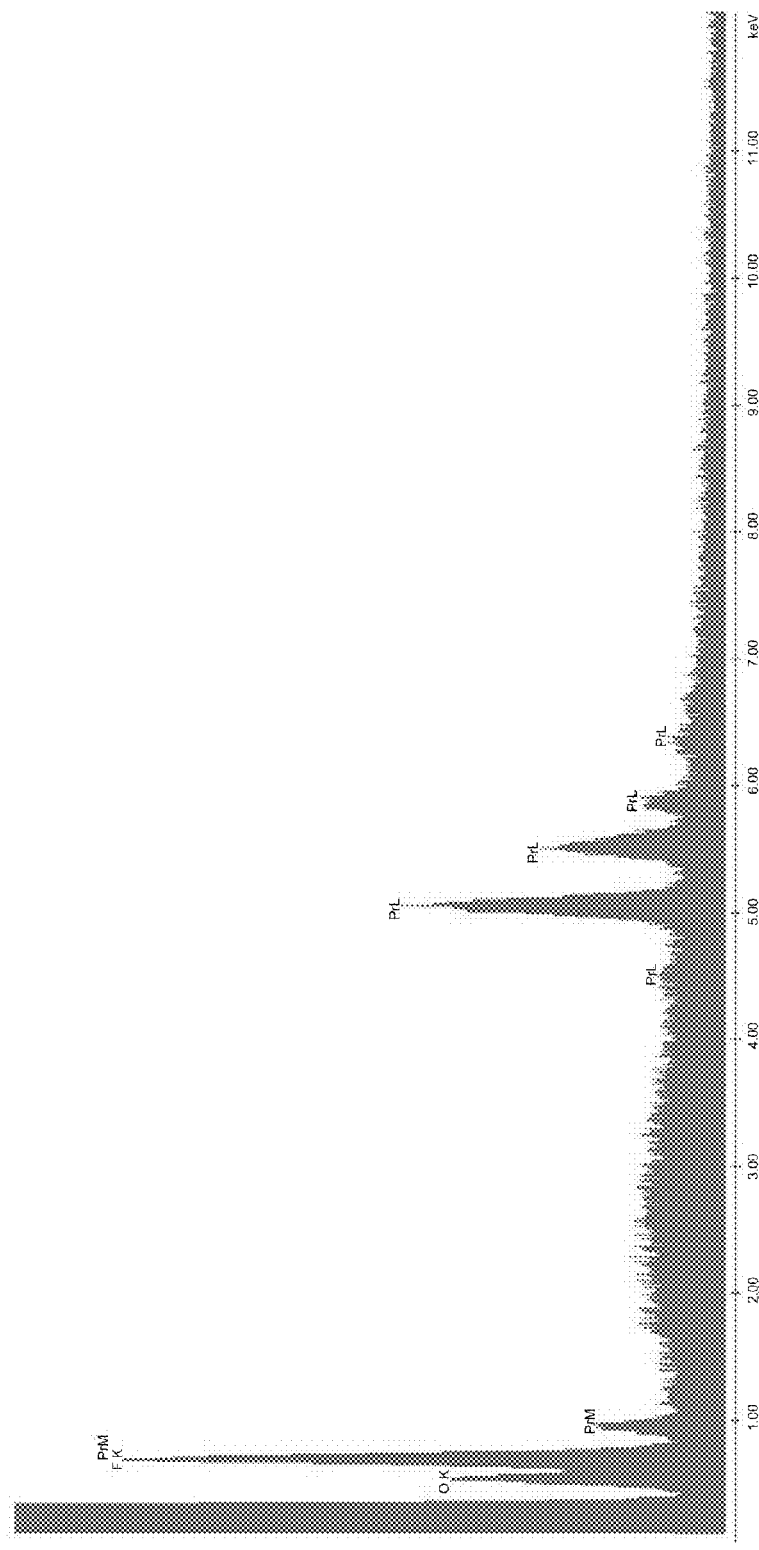
FIG. 8: EDX spectrum.

FIG. 7 shows SEM micrographs of particles as collected from the walls, and also particles dispersed in alcohol after the suspension have been let to settle for one day. Most of the particles have sizes of the order of tens of nanometers and, as we observed in the case of $LaF_3$, several of the particles have sizes in the range 100-200 nm. From the practical point of view, the larger particles can be allowed to settle or centrifuged and only that naturally dispersed particles used for this application. FIG. 8 depicts the EDX spectrum corresponding to an area like the one shown in FIG. 7. As expected, Pr and F peaks are observed, as well as an O peak corresponding to the background (conductive tape).

Example 7

Deca, Centi, Through Mega Parameter Detection on Single Particles Using Mass Spectrometry Traditional flow cytometry allows for fluorescently labeled live cells, fixed cells, beads, or objects (referred herein as mother particles (MP)) to be individually distinguished and separated using cytometric sorting technology based on their fluorescent and light scatter characteristics. This approach is particularly advantageous because it allows for further functional or analytical characterization of individually purified MPs on a phenotypic basis. At the same time, the number of simultaneous parameters that can be measured on a single MP limits this phenotype. In the case of fluorescence, as high as 17 have been reported, however, due to spectral overlap considerations, and a consequent need for a form of correction called "compensation", 10-12 parameters is often thought of as a practical limit.

Elemental mass spectrometry-based flow cytometry (mass cytometry), implemented and established using an instrument (commercial name CyTOF) at the University of Toronto, offers a new approach to analyze MPs via the replacement of fluorochrome-labeled binding reagents (BR—i.e. antibodies, aptamers, chemical linkers, or other affinity reagents) with elemental metal isotope-labeled binding reagents (EmisoL-BR). The MPs to which these EmisoL-BRs bind are then injected into the CyTOF device wherein they are completely atomized, ionized and the resulting elemental metal ions of the (former) EmisoL-BR bound to the MP are mass measured and the individual elemental isotopes are quantified. The relative or absolute number of each isotopic elements associated with each individual MP are then enumerated and stored[3]. Due to the achieved resolution (full width at half-maximum) of mass measurement combined with the number of non-biological rare-earth elemental isotopes available for creating different IsoL-BRs, it is theoretically only possible to measure less than 100 parameters simultaneously on a MP-by-MP basis. The CyTOF device uses an inductively coupled plasma time-of-flight mass spectrometer (ICPTOF-MS), which differs from other MS devices in use for elemental analysis by first, its capability to record mass spectra with 76,400 Hz, allowing to resolve single cell transients, second, its improved ion transmission capabilities and thereby at least ~10-fold increased sensitivity compared to prior ICP-TOF-MS instruments and third and finally, the ability to process and record the generated data stream in real time.

The value of this mass cytometry-based technique, including the routine measurement of 33 parameters, has recently been documented[3-9]. The limitation, however, is that still the number of measurable parameters is limited by the number of available non-biological rare-earth elemental isotopes (approximately 100). For a thorough phenotypic characterization of a single cell hundreds or even thousands of parameters should be ideally measured and quantified. Consequently, all current flow cytometry approaches, including mass cytometry, fall short in yielding a more complete phenotypic signature of single cells. As such, there would be great value in allowing for an approach that overcomes the limitations of measurable parameters set by the availability of non-biological rare-earth elemental isotopes.

Figure 9:
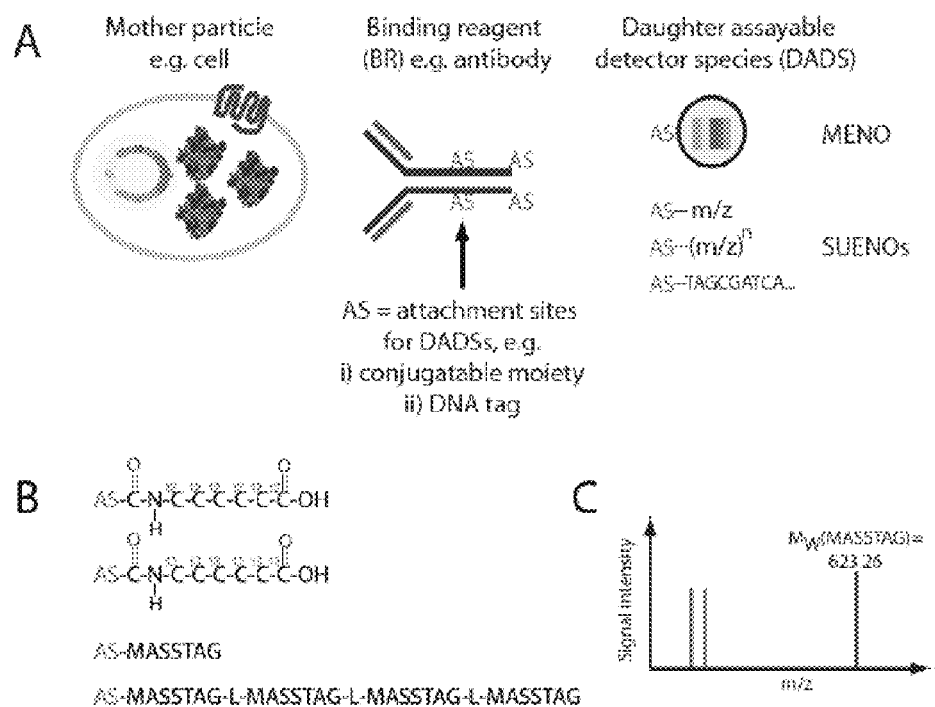
FIG. 9A: Daughter Assayable Detector Species (DADS), which can either be Metal Encoded Nano-Objects (MENOs) or Structural Unit Encoded Nano-Objects-(SUENOs) with definable mass over charge ratios (m/z), are coupled to binding reagents (BR) via attachment sites (AS). The BR specifically recognize and bind epitopes on the mother particle (MP) B. SUENOs with unique mass over charge rations can be small molecule compounds that for example differ in their isotopic composition, small peptide tags (here shown with the amino acid sequence MASSTAG) or polymers consisting of small molecule compounds/peptides linked with specifically cleavable linkers (-L-). C. As a result each SUENO or subunits thereof can be uniquely identified and quantified via its mass to charge ratio.

Terms (FIG. 9A):

MP: Mother Particle. Cell or unit object that hosts or houses multiple epitopes or determinants to be measured.

BR: Binding Reagent. Reagents with specificity for epitopes on the MP, and which have a moiety allowing attachment of a DADS. BRs can be aptamers, antibodies, diabodies, constrained binding loops, or affinity reagents of any kind. Depending on the method used, can either a) harbor a conjugatable moiety for attaching a DADS directly by covalent bond or chelation; b) harbor an attached double strand DNA sequence "bar code" that uniquely identifies the BR distinctly from other BRs; or c) harbor an attached single strand "sense" DNA sequence "bar code" that uniquely identifies the BR distinctly from other BRs.

DADS: Daughter Assayable Detector Species. A unique assayable (i.e. by mass or mass to charge ratio—m/z) species detectable by mass spectrometry. Can be attached directly to a BR via a covalent linkage. Can be attached to a BR via a linker to the bar coded DNA. Can be attached to a BR via a complementary "anti-sense" strand to the "sense" DNA strand (after denaturation to free up the available DNA "sense" strand). Can be attached to a BR via a complementary "anti-sense" strand to the "sense" DNA strand. DADS are either in the current form either MENOs or SUENOs.

MENOs: Metal Encoded Nano-Objects. Nanoscale size particles with defined ratios of 1 or more isotopes. Each nanoparticle's signature ratio is distinct such that it would act as a unique DADS when bound to an BR. To use MENOs, one would create 100s, or 1000s of MENOs with unique signatures. These would be attached to BRs. The entire set of MENOs from a given cell are assayed individually in a manner that allows the cumulative number of given MENOs with a given ratio of elements to be determined on a per cell basis.

Figure 10A:
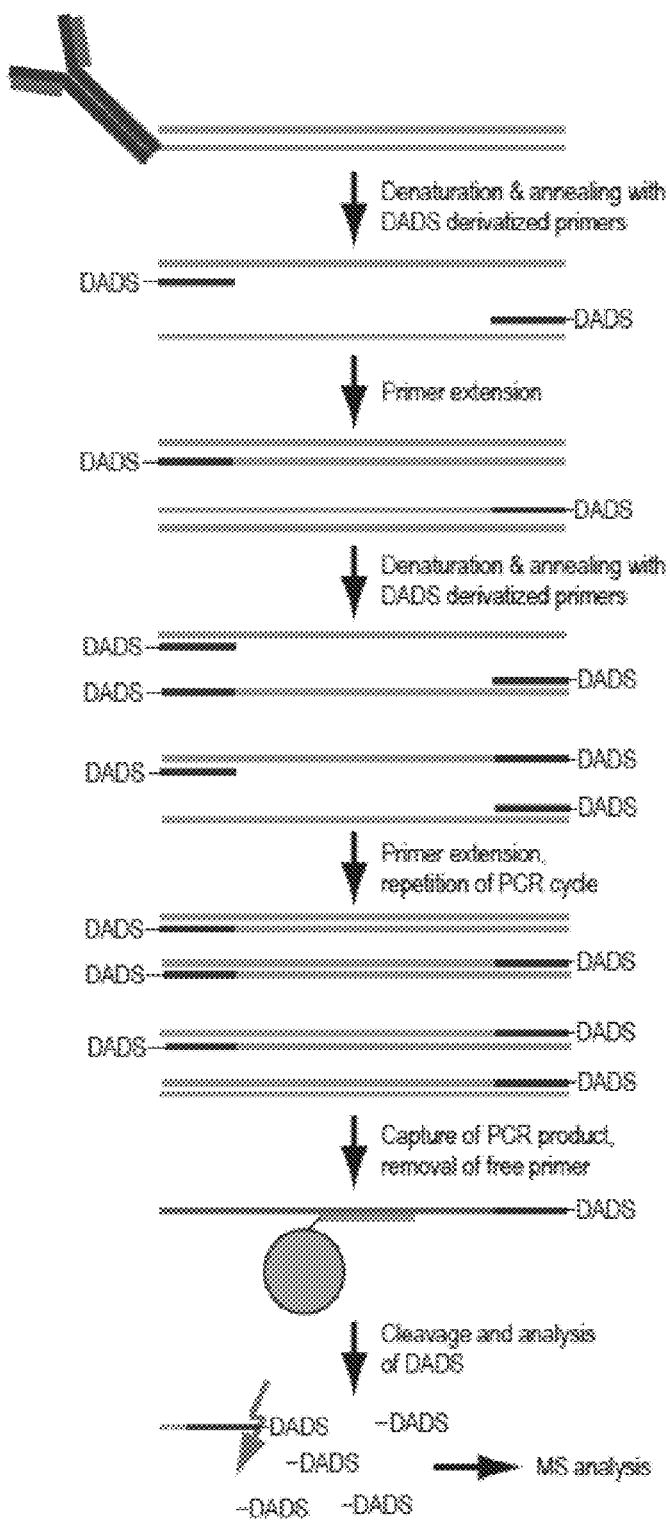
FIG. 10. DADS amplification (in this example the DNA strands are bound to an antibody) A. The DNA tag is amplified by using primers which are coupled to DADS via standard PCR approaches. After n-rounds of amplification the amplified DNA is captured and separated from the free DADS primer. Subsequently the DADS can be cleaved and analyzed using mass spectrometry. B. In an alternative approach, DNA-DADS probes complementary to the amplified DNA strand are added during the PCR reaction. In every PCR cycle, the probe is degraded and the DADS is released. After PCR either the remaining DNA-DADS probes can be captured and subsequently the free DADS can be measured using mass spectrometry.
Figure 10B:
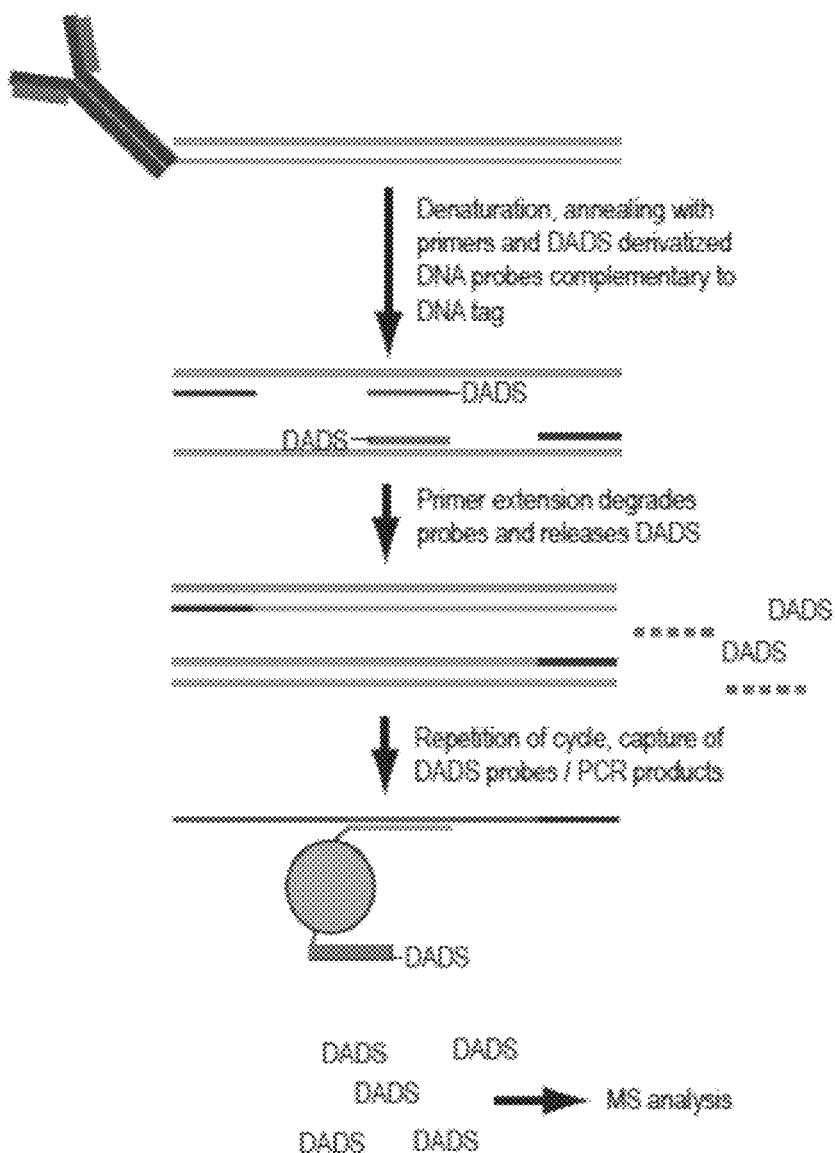

SUENOs: Structural Unit Encoded Nano-Objects (FIGS. 10B & C). A unique molecular weight organic molecule that is detected in mass spectrometry as a distinct species. A SUENO can be: a) a small molecule of a defined molecular weight unique from other SUENOs. b) A polymeric substance of a defined molecular weight unique from other SUENOs. c) A small molecule of a defined molecular weight, or whose derived ions generated during mass spectrometry are uniquely generated or have unique masses and/or charges unique from other SUENOs. d) A polymer of distinct subunits that together have a defined molecular weight, or whose derived (i.e. by collision induced dissociation—CID) ions generated during mass spectrometry are uniquely generated or have unique masses and/or charges unique from other SUENOs.

The approaches of the invention can greatly extend the number of simultaneous measured parameters. All these approaches have in common that multiple individual Daughter Assayable Detector Species (DADS) are bound via a BR to given epitopes on a MP. The DADS can be quantified using MS techniques as they are (1) associated with the MP or (2) can be separated from the MP, measured and registered to the MP they were derived from. In addition, the DADS in (1) or (2) can be amplified before MS analysis to achieve greater sensitivity.

Such assayable objects as DADS can either be Metal Encoded Nano-Objects (MENOs) or Structural Unit Encoded Nano-Objects-(SUENOs) with definable mass over charge ratios (m/z). Both MENOs and SUENOs have in common that 100s, 1000s to millions or any other number of unique distinguishable and detectable species can be created. As a result, the limitations given by the lack of availability of rare-earth metal isotopes is overcome and an unlimited number of phenotypic features can be analyzed per MP (in a preferred case, the MP is a cell) via the MENOs/SUENOs. In addition, by separating the assayable DADS from the MP, we realize an important signal to noise increase, since most cellular constituents that could interfere with the ionization, ion transmission/storage and ion detection (e.g. overlapping the spectral region defined by the DADS) are "left behind" with the MP during the process. The separation further bears the advantage that DADS can be, if e.g. nucleic acids are used as linkers before the final binding event, amplified or otherwise processed prior to the mass measurement, thereby greatly expanding the usable DADS and overcoming detection limits.

Technical Specifications:

Measurement and quantification of DADS by mass spectrometry. Analysis of MENOs. Currently, mass cytometry instruments can detect under optimal conditions 1 out of 10,000 ions of a given metal isotope at a concentration of approximately 0.1 part per trillion, corresponding to a detection limit of ~100 zeptomol. Therefore, if a MENO contains per used metal isotope equal or more than 10,000 atoms, single molecules can be detected on a MP. The MENOs derived from a single MP can be analyzed as described in Bandura et al. Two modes for the analysis of the MENOs exist. (1) The MENOs are separated from the MP as described under J.2.d/e and quantified using mass cytometry or (2) The MENOs are still attached to the MP. In the first variant the MENOs can be separated and analyzed one by one. Alternatively, for both approaches, all MENOs derived from a single MP can be measured concomitantly and the presence of the MPs is mathematically inferred based on the metal isotope composition and corresponding ion counts present in the recorded composite mass spectrum.

Different approaches can be used to separate and align the MPs for a sequential analysis. These include separation by the following: Generating Micro-bubbles; Placement in Microcavities; Dilution; Flow system, e.g. Capillary; Laser guidance; Sonic alignment; Magnetic alignment; Compartmentalization with oil or air; Others well known in the art. The same approaches can also be used to separate the DADS/SUENOs (see below) derived from one MP to ensure their sequential analyses if needed.

Analysis of SUENOs. Current non-ICP-MS set ups can typically detect 1 out of 1,000,000 ions corresponding to a low attomole sensitivity. Therefore, in order to detect a molecule which is present in a cell with 100 copies, a BR has to carry 10,000 SUENOs. To reduce the number of SUENOs which are bound to a MP via the BR and to overcome any detection limits imposed by the sensitivity of a given MS instrument an alternative approach can be taken: Here a barcode on the DADS are amplified prior to their analyses. As there are no upper limits in the amplification of e.g. DNA based DADS the presented approach allows for single molecule detection per MP, irrespective of the sensitivity of the used MS instrument. A wide variety of methods can be used to analyze and quantify the SUENOs using MS. First, the SUENOs have to be ionized. This can be achieved in the gas phase, solid state or in solution, for example by: Electron and chemical ionization; Spray ionization—e.g. electrospray ionization; Desorption ionization—e.g. matrix-assisted laser desorption ionization; Gas discharge ionization; Ambient ionization; Any other used methods to ionize analytes for MS.

Appropriate MS instruments are either able to directly measure and quantify the SUENOs or can be combined with devices which allow to breakdown the DADS into the SUENOs (see J.2.d/e) and allowing for the sensitivity and scanning speed to detect the SUENOs of single MPs. The following mass analyzers can be used to determine the m/z of the SUENOs: Time of flight (TOF); Quadrupole; Ion trap; Fourier transform ion cyclotron resonance; Orbitrap; Sector; Any other mass analyzer; And combinations thereof. One MS instrument set-up which is particularly suitable to measure and quantify the SUENOs is a quadrupole-time of flight MS. It achieves low attomole sensitivity, allows detecting transients of single MPs due to the high scanning speed and can either be directly used to break down the DADS into SUENOs via collision induced dissociation (CID) or can be easily interfaced with additional instruments needed to e.g. break down the DADS into the SUENOs. Another instrument set-up exploits laser ionizable SUENOs derived from a MP. The SUENOS from a given MP are either already located (see H.1) or can be deposited on a chip and MALDI is used to ionize them. If the DADS also consist of SUENOs linked via UV or acid sensitive linkers to the MP, the DADS are concomitantly broken down into their SUENOs. The ions are preferably detected using a TOF instrument.

Amplification of DADS and subsequent analysis using mass spectrometry. The DNA signature of the DADS can either be amplified in the gas, solid or liquid phase. The amplification process can be performed in a mixture of MPs if no cross-talk between the MP-BR-DADS is possible. Otherwise, the MPs are in localizable reaction chambers separated from each other to perform manipulation of the DADS. These reaction chambers can be in the solid, gas or liquid phase, for example on/in: Microarray; Microfluidics device; Emulsions (e.g. water-oil); Droplets in gas phase; Any other technique which allows the separation needed to amplify the DADS.

Alternatively, the DADS can be first separated from the MPs as described above before amplification. By using standard molecular biology approaches (such as frequently employed in emulsion polymerase chain reactions (PCR) the DNA-DADS present in the reaction chamber are amplified using primers which carry a unique non-DNADADS. After amplification, DNA sequences complementary to the DNA-DADS (but different from the primer sequence) are used to capture and retain the reaction product in the reaction chamber while all left over primers are removed. This can e.g. be achieved with magnetic beads or with the microarray wells spotted with the complementary DNA strands. In the last step, the DADS are released from the DNA strands. Alternatively, an approach analogous to the commonly used real time PCR method using a "Tag-man probe" can be employed: besides the primers needed to amplify the DNA-DADS, a short DNA probe complementary to the DNA-DADS can be added during amplification. This probe is coupled to an non-DNA-DADS. If the target sequence is present, the DNA sequences anneal and by using polymerases with 5'-3' exonuclease activity, the probe is degraded during amplification in every round of PCR, thereby releasing the non-DNA-DADS. As a result in both cases free DADS are generated which can be directly analyzed, separated into the SUENOs or separated from the MP and measured as described above.

Generation and Manipulation of DADS.

The MENOs attached to the MPs are nanoparticles or particles of any other size with a defined combination and number of metal isotopes. As such n100 different particles can be generated (100 is the number of available metal isotopes measurable by CyTOF and "n" describes the number of distinct molar quantities (relative to an internal standard per particle). Even if the nanoparticles are generated by using each metal in a digital manner (present or not present) 2100 unique particles can be generated.

MENOs can be generated in a variety of manners: (1) Cooled vapor deposition (CVD) of heated ratiometrically determined mixtures of isotopes to crystalline or other solid-packed forms. (2) Liquid phase condensation of dissolved ratiometrically determined mixtures of isotopes with appropriate salts or conditions to create a crystal structure of appropriate final ratios. (3) Layering of pure or ratiometrically determined mixtures of isotopes to attain a final ratiometrically determined mixture of isotopes in a given nanoparticle. 3. In a final step MENOs are treated, or made, with a tagging group that directly, or indirectly, allows for their attachment to a BR.

SUENOs with a defined mass to charge ratio. 1. An alternative DADS consists of SUENOs to detect and quantify epitopes present on the MPs. Each SUENO has a defined and unique m/z and can be specifically released from the MP and is subsequently injected into a more "standard" MS instrument, where it is detected and measured relative or absolutely quantified. To increase the sensitivity of the detected targets, the DADS can be provided as a polymer of detectable SUENOs that, in the monomeric form are 1%, 10%, 100% or any other percentage ionized. Alternatively, the DADS and/or SUENOs can be amplifiable. In either event, the SUENO is the detected unit in the MS.

Generation of DADS-BR: a) First, each BR is labeled with a DADS/SUENO, which can be a: (1) Small molecule compound; (2) Amino acid; (3) Peptide; (4) Nucleotide; (5) DNA; (6) RNA; (7) Metabolite; (8) Mono-saccharide; (9) Poly-saccharide; (10) Any other sort of enzyme cleavable substrate; (11) Metalo-organic compound; (12) Any other chemically producible compound; (13) Any combination of the above mentioned. Alternatively, in order to increase the number of ions bound to a BR, the BR can be labeled with DADS composed of SUENOs, such as a polymer (or variants thereof such as dendrimers), consisting of the compounds mentioned above.

Different forms of linkers can be used to connect the SUENOs into the DADS. These include: (1) Covalent linkers as (used in protein chemistry), including Peptide bonds; Nucleotide-nucleotide bonds; Small molecules; Acid/base labile bonds; Electromagnetic labile bonds; Electron-radical labile bond; DNA; Peptide; Saccharides; Polyethylene glycol (PEG); Any other sort of enzyme cleavable substrate; Or any other linker. Alternatively affinity based linkers may be used, e.g. Biotin-streptavidin; Protein A or G or L; Calmodulin; Glutathione S-transferase; Poly-Histidine; Peptide tags (e.g. FLAG-tag); Metal affinity based linkers; Or any other affinity based linker.

The linkers between the SUENOs are cleavable by any rapid inducible separation technique, including; (1) Chemical; (2) Mechanical; (3) Enzymatic; (4) Sonic; (5) Electromagnetic methods; (6) Any other method; e) If the linkers between the SUENOs are broken down within the mass spectrometer, the separation methods can more specifically include (1) Collision induced dissociation; (2) Infrared multiphoton dissociation; (3) Blackbody infrared radiative dissociation; (4) Electron-capture dissociation; (5) (Negative) electron-transfer dissociation; (6) Electron-detachment dissociation; (7) Surface induced dissociation.

The cleavage either adds or subtracts a defined number of charges to/from each SUENO or does not alter the charge state at all. The cleavage can happen in the gas, liquid or solid phase.

The DADS can be broken down into the SUENOs in gas, liquid or solid phase, while (1) in the reaction chamber; (2) still attached to the MP and transported to the MS; (3) injected into the MS instrument; (4) in the MS instrument.

Each SUENO has a defined and distinct m/z and can be singly-, doubly-, triply- or n-times charged, depending on the design of the experimental detection protocol. The SUENO can be any of the compounds as described for the DADS. To increase the number of producible DADS and therefore measurable parameters the SUENOs can be synthesized with defined isotopes of any existing element yielding SUENOs with 1 or n Dalton mass differences that allow to uniquely identify and quantify them in a MS measurement, therefore their mass difference will be defined by the achievable resolution of the MS instrument. Preferred elements with their isotopes are (1) hydrogen; (2) carbon; (3) nitrogen; (4) oxygen; (5) chlorine; (6) fluorine; (7) bromide; (8) any other available element and its isotopes that can be synthesized into an SUENO. Similarly, only a unique DNA sequence is attached to the BR and used to stain the MPs, allowing for further amplification of the DADS.

Staining/labeling of MPs with DADS/SUENO-BRs: The staining of MPs with DADS-BRs or SUENO-BRs follows standard staining protocols for antibodies (as BRs) to cells. The following references contain exemplary staining protocols: 1. Fluorescent cell barcoding for multiplex flow cytometry. Krutzik P O, Clutter M R, Trejo A, Nolan G P. Curr Protoc Cytom. 2011 January; Chapter 6:Unit 6.31. Phospho flow cytometry methods for the analysis of kinase signaling in cell lines and primary human blood samples. Krutzik P O, Trejo A, Schulz K R, Nolan G P. Methods Mol Biol. 2011; 699:179-202. Duration of antigen receptor signaling determines T-cell tolerance or activation. Katzman S D, O'Gorman W E, Villarino A V, Gallo E, Friedman R S, Krummel M F, Nolan G P, Abbas A K. Proc Natl Acad Sci USA. 2010 Oct. 19; 107(42):18085-90. Epub 2010 Oct. 4. Tyramide signal amplification for analysis of kinase activity by intracellular flow cytometry. Clutter M R, Heffner G C, Krutzik P O, Sachen K L, Nolan G P. Cytometry A. 2010 November; 77(11):1020-31. B-cell signaling networks reveal a negative prognostic human lymphoma cell subset that emerges during tumor progression. Irish J M, Myklebust J H, Alizadeh A A, Houot R, Sharman J P, Czerwinski D K, Nolan G P, Levy R. Proc Natl Acad Sci USA. 2010 Jul. 20; 107(29):12747-54. Epub 2010 Jun. 11. New technologies for autoimmune disease monitoring. Maecker H T, Nolan G P, Fathman C G. Curr Opin Endocrinol Diabetes Obes. 2010 August; 17(4):322-8. Review. Characterization of patient specific signaling via augmentation of Bayesian networks with disease and patient state nodes. Sachs K, Gentles A J, Youland R, Rani S, Irish J, Nolan G P, Plevritis S K. Conf Proc IEEE Eng Med Biol Soc. 2009; 2009:6624-7.

Methods to couple and separate DADS from the MPs 1. The DADS are coupled to the MPs such that they allow for the direct analysis using MS or alternatively, are separated from the MP for further manipulation (such as amplification) needed for the subsequent MS quantification. 2. The DADS can be linked to the BR. 3. In order to release the DADS from the BR, the methods as described above can be employed. 4. The DADS can be released from the BR in the gas phase, solid state or in solution. 5. Depending on the methods used to release and separate the DADS from the MP, distinct methods can be employed to ensure that a given MS spectrum can be assigned to a MP. a) In case the DADS was separated from the BR in the solid phase, the coordinates of the MP position can be used to assign a MS spectrum to the MP.

In case the DADS is decoupled and separated from the MP in a liquid microsphere (e.g. emulsion, microfluidics device, droplets in gas phase), then the exact location of the release transfer must be known as well as a) the accurate time to the MS analysis of the DADS and b) the accurate time at which the MP is further process (e.g. sorted). Importantly, time in a)>b) to allow for the data processing of the MS spectrum and controlling the destiny of the MP. a) To ensure an accurate timing, e.g. bifunctional fluorescent-DADS calibration beads can be added to the microcavities. Thereby a) and b) can be calibrated in real time.

In an example set up, the BR could be coupled to a short DNA tether by standard chemical approaches, and then coupled to the DADS. Similarly, the above described DNA tethers are only used to tie/decouple the binding reagent to the DADS. This "tri" reagent is then used to stain the MPs. To 'decouple' the BR from the DADS and to generate the quantifiable SUENOs, one would use DNAse which specifically cleaves DNA and would release the BR from the DADS and also generates the SUENOs.

Preferred set-ups a) Separation and amplification b) MENOs or SUENOs Direct measurement of DADS In a preferred configuration, the DADS are not naturally occurring DNA sequences and are attached to BRs. These DADS-BRs are used to stain the cells and the unbound DADS-BR reagents are removed. Subsequently, the MPs are separated from each other into distinct reaction chambers using a hydrocarbon/water emulsion and the bound DADS are amplified. In the final step the DADS are analyzed by mass spectrometry.

References: Herzenberg, L. A. et al. The history and future of the fluorescence activated cell sorter and flow cytometry: a view from Stanford. *Clin. Chem* 48, 1819-1827 (2002); Perfetto, S. P., Chattopadhyay, P. K. & Roederer, M. Seventeen-colour flow cytometry: unraveling the immune system. *Nature Rev. Immunol.* 4, 648-655 (2004); Bandura, D. R. et al. Mass Cytometry Technique for Real Time Single Cell Multitarget Immunoassay Based on Inductively Coupled Plasma Time-of-Flight Mass Spectrometry. *Anal. Chem* (2009).doi: 10.1021/ac901049w; Razumienko, E. et al. Element-tagged immunoassay with ICP-MS detection: evaluation and comparison to conventional immunoassays. *J. Immunol. Methods* 336, 56-63 (2008); Ornatsky, O. I. et al. Study of cell antigens and intracellular DNA by identification of element-containing labels and metallointercalators using inductively coupled plasma mass spectrometry. *Anal. Chem* 80, 2539-2547 (2008). 6. Ornatsky, O. I. et al. Development of analytical methods for multiplex bio-assay with inductively coupled plasma mass spectrometry. *J Anal At Spectrom* 23, 463-469 (2008); Ornatsky, O., Baranov, V. I., Bandura, D. R., Tanner, S. D. & Dick, J. Multiple cellular antigen detection by ICP-MS. *J. Immunol. Methods* 308, 68-76 (2006); Baranov, V. I., Quinn, Z., Bandura, D. R. & Tanner, S. D. A sensitive and quantitative element-tagged immunoassay with ICPMS detection. *Anal. Chem* 74, 1629-1636 (2002); Bendall S C, Simonds, Qiu Amir E D, Krutzik P O, Finck R, Bruggner R V, Melamed R, Trejo A, Ornatsky O I, Balderas R S, Plevritis S K, Sachs K, Pe'er D, Tanner S D & Nolan G P. Single-cell Mass Cytometry of Differential Immune and Drug Responses Across a Human Hematopoietic Continuum. *Science* In Press; Williams, R., Peisajovich, S. G., Miller, O. J., Magdassi, S., Tawfik, D. S. & Griffiths A. D. Amplification of complex gene libraries by emulsion PCR. *Nat. Methods* 7, 545-50 (2006); Holland, P. M., Abramson, R. D., Watson, R., & Gelfand, D. H. Detection of specific polymerase chain reaction product by utilizing the 5'-3' exonuclease activity of *Thermus aquaticus* DNA polymerase. *PNAS* 88, 7276-80 (1991).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, medicine, and molecular biology or related fields are intended to be within the scope of the following claims.

What is claimed is:

1. A probe comprising a specific binding member for an analyte, conjugated at a single linkage site to a mass dot, wherein the mass dot is a solid lanthanide metal particle of at least 100 metal atoms, free of high atomic mass dopants, and having an isotopic purity between about 90 and 100%.

2. The probe of claim 1 wherein said mass dot is at least about $10^3$ lanthanide metal atoms.

3. The probe of claim 1, wherein said mass dot is at least about $10^4$ lanthanide metal atoms.

4. A probe comprising a specific binding member for an analyte, conjugated at a single linkage site to a mass dot, wherein the mass dot is a solid lanthanide particle of at least 100 metal atoms, free of high atomic mass dopants, wherein said mass dot is comprised of non-fluorescent nanocrystal of two or more lanthanide metals at a known ratio and absolute quantity.

5. The probe of claim 1, wherein said mass dot solid lanthanide particle is in nanocrystal form.

6. A probe comprising a specific binding member for an analyte, conjugated at a single linkage site to a mass dot, wherein the mass dot is a solid lanthanide particle of at least 100 metal atoms, free of high atomic mass dopants, wherein said mass dot comprises a nanoparticle core of said lanthanide metal, and a low molecular weight counter-anion of a molecular weight outside the detection range of ICP-MS.

7. The probe of claim 1, wherein said mass dot comprises a coating selected from an amphipathic polymer, PEG, silane, siloxane, silica, or lipids.

8. The probe of claim 1, wherein a single mass dot is conjugated to said specific binding member.

9. The probe of claim 1, wherein not more than 10 mass dots are conjugated to said specific binding member.

10. The probe of claim 8, wherein said specific binding member is a polypeptide.

11. The probe of claim 10, wherein said specific binding member is an antibody.

12. The probe of claim 8, wherein said specific binding member is a polynucleotide.

13. The probe of claim 8, wherein said specific binding member is avidin or streptavidin.

14. A method for the detection of an analyte, the method comprising:
  binding said analyte through specific binding to a probe as set forth in claim 1; and detecting the presence of said mass dot.

15. A method for the detection of an analyte, the method comprising:
  binding the analyte through specific binding to 10 or more distinct probes, wherein each probe comprises a specific binding member conjugated at a single linkage site to at least one mass dot and not more than 10 mass dots, wherein the mass dot is a solid lanthanide particle of at least 100 metal atoms, free of high atomic mass dopants, and having an isotopic purity between about 90 and 100%,
  wherein said detecting is performed by ICP-MS with solution analysis or by mass cytometry.

16. The method of claim 15, wherein the detecting is performed by mass cytometry.

* * * * *